(12) United States Patent
Gin et al.

(10) Patent No.: US 8,454,895 B2
(45) Date of Patent: Jun. 4, 2013

(54) ONLINE CONTAMINANT DETECTION AND REMOVAL SYSTEM

(75) Inventors: Karina Yew-Hoong Gin, Singapore (SG); Trevor R. Garrett, Brussels (BE)

(73) Assignee: Nanyang Technological University, Singapore (SG)

( * ) Notice: Subject to any disclaimer, the term of this patent is extended or adjusted under 35 U.S.C. 154(b) by 609 days.

(21) Appl. No.: 12/598,627

(22) PCT Filed: May 2, 2008

(86) PCT No.: PCT/SG2008/000156
§ 371 (c)(1),
(2), (4) Date: Jan. 26, 2010

(87) PCT Pub. No.: WO2008/136769
PCT Pub. Date: Nov. 13, 2008

(65) Prior Publication Data
US 2010/0133200 A1    Jun. 3, 2010

Related U.S. Application Data

(60) Provisional application No. 60/915,718, filed on May 3, 2007.

(51) Int. Cl.
*G01N 33/53* (2006.01)
*G01N 33/533* (2006.01)

(52) U.S. Cl.
USPC .... 422/82.08; 422/400; 422/68.1; 422/82.05; 435/5; 436/63; 436/518; 436/523; 436/527; 436/531; 436/800; 436/805; 210/94; 210/742; 210/743; 210/745

(58) Field of Classification Search
USPC ............... 435/5; 436/63, 518, 523, 526, 527, 436/531, 800, 805; 422/63, 68.1, 82.05, 82.08, 422/400, 403; 210/94, 742, 743, 745
See application file for complete search history.

(56) References Cited

U.S. PATENT DOCUMENTS

| 4,336,337 A | 6/1982 | Wallis et al. |
| 5,081,017 A | 1/1992 | Longoria |

(Continued)

FOREIGN PATENT DOCUMENTS

| CA | 2 547 489 | 11/2006 |
| DE | 19 641 876 | 4/1998 |

(Continued)

OTHER PUBLICATIONS

Ammor, "Recent advances in the use of intrinsic fluorescence for bacterial identification and characterization", *J. Fluoresc.*, 17:455-459 (2007).

(Continued)

*Primary Examiner* — Duane Smith
*Assistant Examiner* — Paul J Durand
(74) *Attorney, Agent, or Firm* — Pabst Patent Group LLP

(57) ABSTRACT

This invention refers to continuous flow devices for detecting and/or removal of contaminants from a liquid stream. The device comprises a cartridge with an inlet and outlet for the liquid stream, a radiation incident and emerging wall portion and optically transparent support material packed in the cartridge such that a liquid stream can pass between voids or spaces formed within the optically transparent material, as well as a radiation source and detector. The support material comprises molecules for capturing at least one contaminant on the surface of the support material and each of the capture molecules comprises at least one reporter group which emits a signal upon binding of the contaminant. Another form of the invention refers to a rotatable support within the liquid stream.

21 Claims, 17 Drawing Sheets

U.S. PATENT DOCUMENTS

| | | | |
|---|---|---|---|
| 5,159,398 | A | 10/1992 | Maekawa et al. |
| 5,159,403 | A | 10/1992 | Kosaka |
| 5,380,873 | A | 1/1995 | Bieniarz et al. |
| 6,017,440 | A | 1/2000 | Lewis et al. |
| 6,022,951 | A | 2/2000 | Sano et al. |
| 6,103,493 | A | 8/2000 | Skerra et al. |
| 6,451,536 | B1 | 9/2002 | Fodor et al. |
| 6,473,171 | B1 | 10/2002 | Buttry et al. |
| 6,576,424 | B2 | 6/2003 | Fodor et al. |
| 6,589,792 | B1 | 7/2003 | Malachowski |
| 6,630,299 | B2 | 10/2003 | Carrion et al. |
| 6,642,018 | B1 | 11/2003 | Koller et al. |
| 6,656,683 | B1 | 12/2003 | Reuben et al. |
| 7,601,803 | B1 | 10/2009 | Fiedler et al. |
| 2006/0160086 | A1 | 7/2006 | Volland et al. |

FOREIGN PATENT DOCUMENTS

| | | |
|---|---|---|
| JP | 2006017736 | 1/2006 |
| JP | 2006149215 | 5/2006 |
| WO | WO 86/02077 | 4/1986 |
| WO | WO 96/23879 | 8/1996 |
| WO | WO 96/24606 | 8/1996 |
| WO | WO 97/35189 | 9/1997 |
| WO | WO 98/40396 | 9/1998 |
| WO | WO 01/04144 | 1/2001 |
| WO | WO 02/077018 | 10/2002 |
| WO | WO 03/029462 | 4/2003 |
| WO | WO 2004/048936 | 6/2004 |

OTHER PUBLICATIONS

Ammor, et al., "Reagentless identification of human bifidobacteria by intrinsic fluorescence", *Journal of Microbiological Methods*, 69:100-106 (2007).

Argarana, et al., "Molecular cloning and nucleotide sequence of the streptavidin gene", *Nucleic Acids Res*. 14(4):1871-1882 (1986).

Arunachalam, et al., "Monitoring aerobic sludge digestion by online scanning fluorometry", *Water Research*, 39:1205-1214 (2005).

Beste, et al., "Small antibody-like proteins with prescribed ligand specificities derived from the lipocalin fold", *Proc. Natl. Acad. Sci. USA*, 96:1898-1903 (1999).

Billinton and Knight, "Seeing the wood through the trees: a review of techniques for distinguishing green fluorescent protein from endogenous autofluorescence", *Analytical Biochemistry*, 291:175-197 (2001).

Boehm, et al., "On-chip microfluidic biosensor for bacterial detection and identification", *Sensors and Actuators B*, 126:508-514 (2007).

Boltasseva and Shalaev, "Fabrication of optical negative-index metamaterials: recent advances and outlook", *Metamaterials*, (2008), doi:10.1016/j.metmat.2008.03.004.

Bunka and Stockley, "Aptamers come of age—at last", *Nat. Rev. Microbiol.*, 4:588-596 (2006).

Carothers, et al., "Informational complexity and functional activity of RNA structures", *J. Am. Chem. Soc.*, 126(16):5130-7 (2004).

Chen, at al., "Exploring bioaugmentation strategies for azo-dye decolorization using a mixed consortium of *Pseudomonas luteola* and *Escherichia coli*", *Process Biochemistry*, 41:1574-1581 (2006).

Deisingh and Thompson, "Detection of infectious and toxigenic bacteria", *Analyst*, 127:567-581 (2002).

Deisingh, "Biosensors for microbial detection", *Microbiologist*, 30-34 (2003).

Dwarakanath, et al., "Quantum dot-antibody and aptamer conjugates shift fluorescence upon binding bacteria", *Biochemical and Biophysical Research Communications*, 325:739-743 (2004).

Farabegoli, et al., "Study on the use of NADH fluorescence measurements for monitoring wastewater treatment systems", *Water Research*, 37:2732-2738 (2003).

Garrett, et al, "Characterization of bacterial adhesion and removal in a flow chamber by micromanipulation measurements", *Biotechnol. Lett*, 30:427-433 (2008).

Giana, et al., "Rapid identification of bacterial species by fluorescence spectroscopy and classification through principal components analysis", *Journal of Fluorescence*, 13(6):489-493 (2003).

Gilbride, et al., "Molecular techniques in wastewater: understanding microbial communities, detecting pathogens, and real-time process control", *Journal of Microbiological Methods*, 66:1-20 (2006).

Gill and Damle, "Biopharmaceutical drug-discovery using novel protein scaffolds",*Current Opinion in Biotechnology*, 17:653-658 (2006).

Glasgow, et al., "Real-time remote monitoring of water quality: a review of current applications, and advancements in sensor, telemetry, and computing technologies", *Journal of Experimental Marine Biology and Ecology*, 300:409-448 (2004).

Gomez, et al., "Immobilization of peroxidases on glass beads: an improved alternative for phenol removal", *Enzyme and Microbial Technology*, 39:1016-1022 (2006).

Gubala, "Multiplex real-time PCR detection of *Vibro cholerae*", *Journal of Microbiological Methods*, 65:278-293 (2006).

Holt, et al., "Domain antibodies: proteins for therapy", *Trends in Biotechnology*, 21(11):484-490 (2003).

Hoppe-Seyler and Butz, "Peptide aptamers: powerful new tools for molecular medicine", *J. Mol. Med.*, 78(8):426-430 (2000).

Illiades, et al., "Triabodies: single chain Fv fragments without a linker form trivalent trimers" *FEBS Lett.*, 409(3):437-441 (1997).

Iqbal, et al., "A review of molecular recognition technologies for detection of biological threat agents", *Biosensors & Bioelectronics*, 15:549-578 (2000).

Ivnitski, et al., "Biosensors for detection of pathogenic bacteria", *Biosensors & Bioelectronics*, 14:599-624 (1999).

Joachimsthal, et al., "Flow cytometry and conventional enumeration of microorganisms in ships' ballast water and marine samples", *Marine Pollution Bulletin*, 46:308-313 (2003).

Ko and Grant, "Development of a novel FRET method for detection of *Listeria* or *Salmonella*" *Sensors and Actuators B*, 96:372-378 (2003).

Kwon and Kodadek, "Quantitative evaluation of the relative cell permeability of peptoids and peptides",*J. Am. Chem. Soc.*, 129:1508-1509 (7 pages) (2007).

Lagally, et al., "Integrated portable genetic analysis microsystem for pathogen/infectious diseases detection", *Anal. Chem.*, 76(11):3162-3170 (2004).

Lazcka, et al., "Pathogen detection: a perspective of traditional methods and biosensors", *Biosensors and Bioelectronics*, 22:1205-1217 (2007).

Monici, "Cell and tissue autofluorescence research and diagnostic applications", *Biotechnol. Annu. Rev.*, 11:227-56 (2005).

Mosavi, et al., "The ankyrin repeat as molecular architecture for protein recognition", Protein Science, 13(6):1435-1448 (2004).

Napolitano, et al., "Glubodies: randomized libraries of glutathione transferase enzymes", *Chemistry & Biology*, 3(5):359-367 (1996).

Natali and Sampietro, "Detectors based on organic materials: status and perspectives", *Nuclear Instruments and Methods in Physics Research A*, 512:419-426 (2003).

Noble and Weisberg, "A review of technologies for rapid detection of bacterial in recreational waters", *Journal of Water and Health*; 03.4:381-392 (2005).

Oh, et al., "Surface Plasmon resonance immunosensor for the detection of *Yersinia enterocolitica*", *Colloids Surfaces A: Physicochem. Eng. Aspects*, 257-258:369-374 (2005).

Rompré, et al., "Detection and enumeration of coliforms in drinking water: current methods and emerging approaches", *Journal of Microbiological Methods*, 49:31-54 (2002).

Sanders and Manz, "Chip-based Microsystems for genomic and proteomic analysis", *Trends in Analytical Chemistry*, 19(6):364-378 (2000).

Shalaev, "Optical negative-index metamaterials", *Nature photonics*, 1:41 (2007).

Shokoohi, et al., "Silane Coupling agents in polymer-based reinforced composites: a review", *Journal of Reinforced Plastics and Composites*, 27(5):473-485 (2008).

Silverman, et al., "Multivalent avimer proteins evolved by exon shuffling of a family of human receptor domains", *Nature Biotechnology*, 23(12):1556-1561 (2005).

Singh, et al., "Development of sensors for direct detection of organophosphates. Part I: immobilization, characterization and stabilization of acetylcholinesterase and organophosphate hydrolase on silica supports", *Biosensors & Bioelectronics*, 14:703-713 (1999).

Skerra, "Engineered protein scaffolds for molecular recognition", *J. Mol. Recognit.*, 3:167-187 (2000).

Stone, et al., "The assembly of single domain antibodies into bispecific decavalent molecules", *Journal of Immunological Methods*, 318:88-94 (2007).

Straub and Chandler, "Towards a unified system for detecting waterborne pathogens", *Journal of Microbiological Methods*, 53:185-197 (2003).

Tang, et al., "High-temperature fluorescent in situ hybridization for detecting *Escherichia coli* in seawater samples, using rRNA-targeted oligonucleotide probes and flow cytometry", *Applied and Environmental Microbiology*, 71(12):8157-8164 (2005).

Tombelli, et al., "Analytical applications of aptamers", *Biosensors and Bioelectronics*, 20:2424-2434 (2005).

Van Emon, et al., "Bioseparation and bioanalytical techniques in environmental monitoring", *Journal of Chromatography B*, 715:211-228 (1998).

Wos and Pollard, "Sensitive and meaningful measures of bacterial metabolic activity using NADH fluorescence", *Water Research*, 40:2084-2092 (2006).

Wu, et al., "Real-time detection of *Escherichia coli* O157:H7 sequences using a circulating-flow system of quartz crystal microbalance", *Biosensors and Bioelectronics*, 22:2967-2975 (2007).

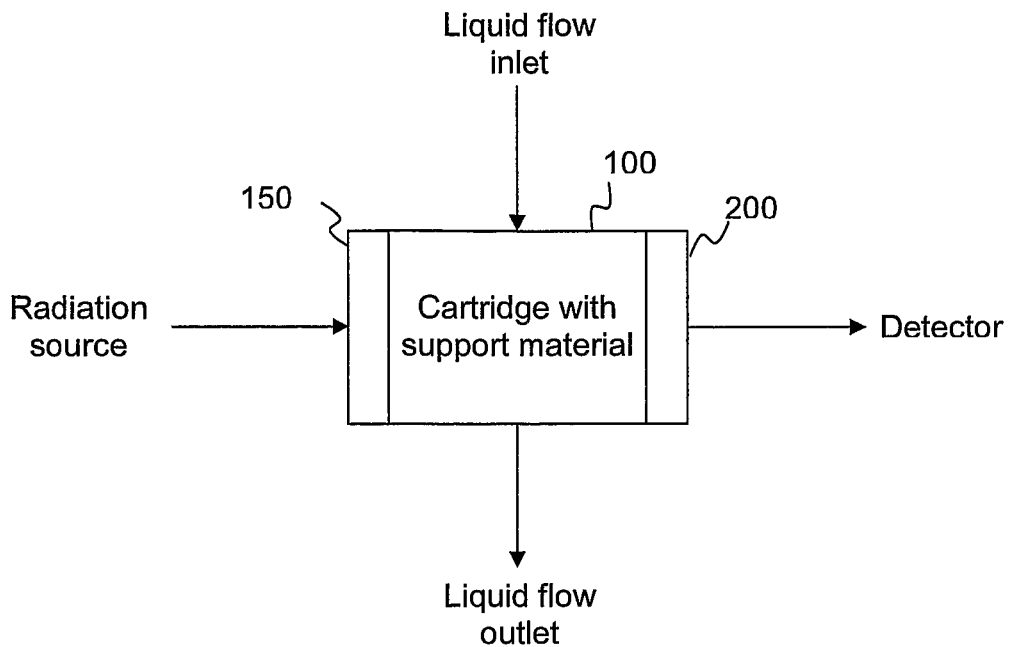
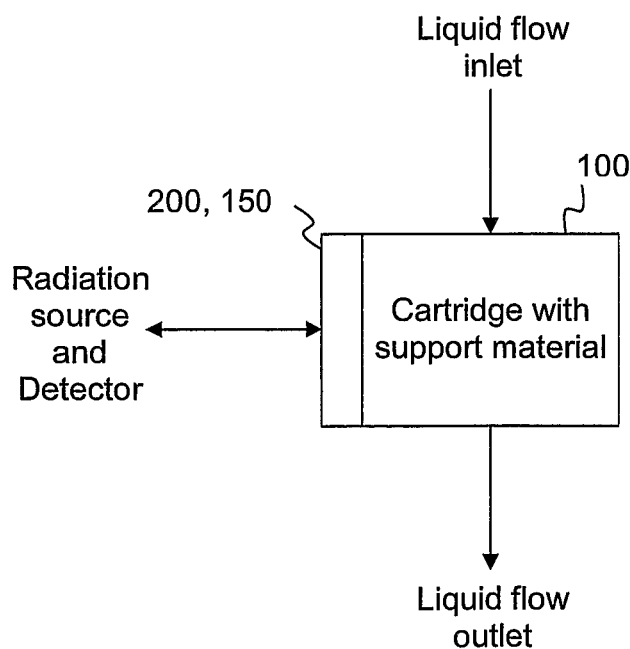

FIG.3A I
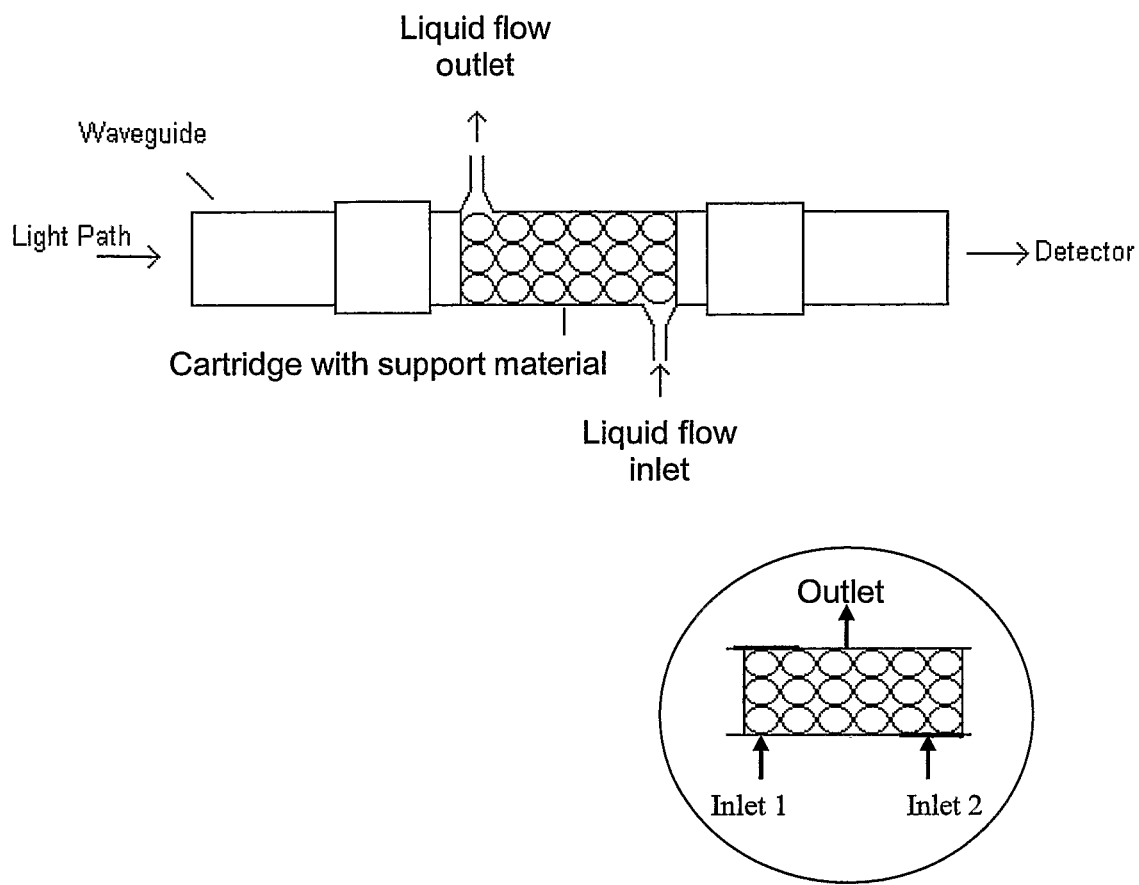
FIG. 3A II
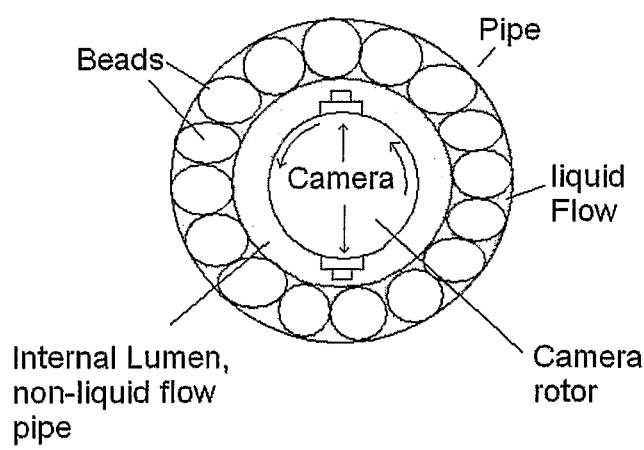

Cartridge with
support material

FIG. 13/1
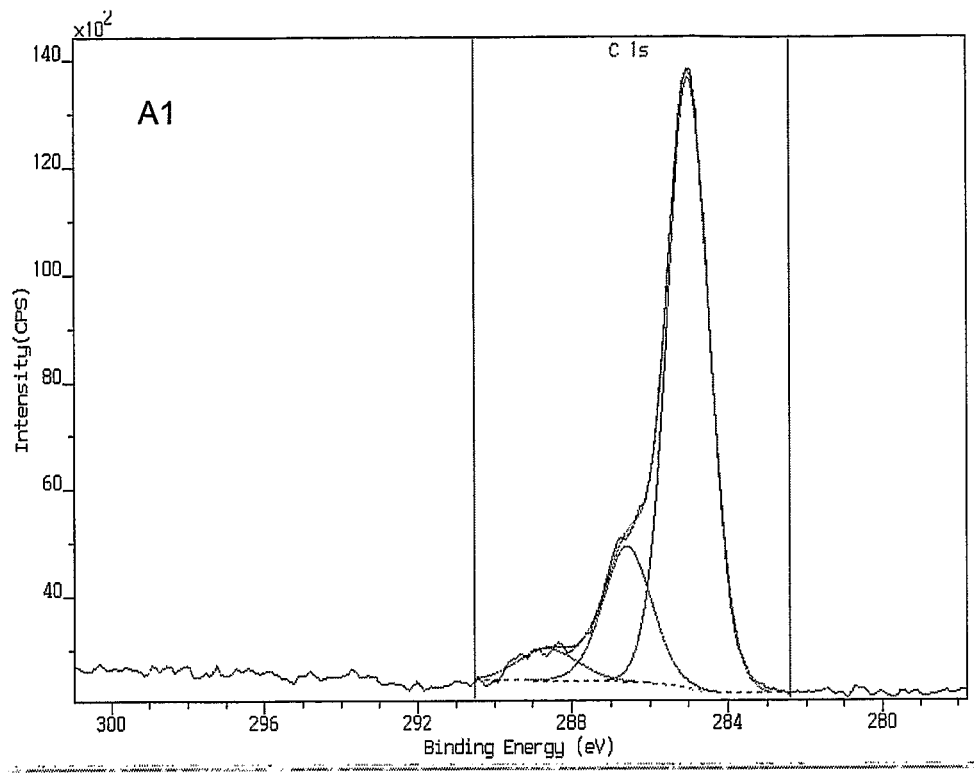
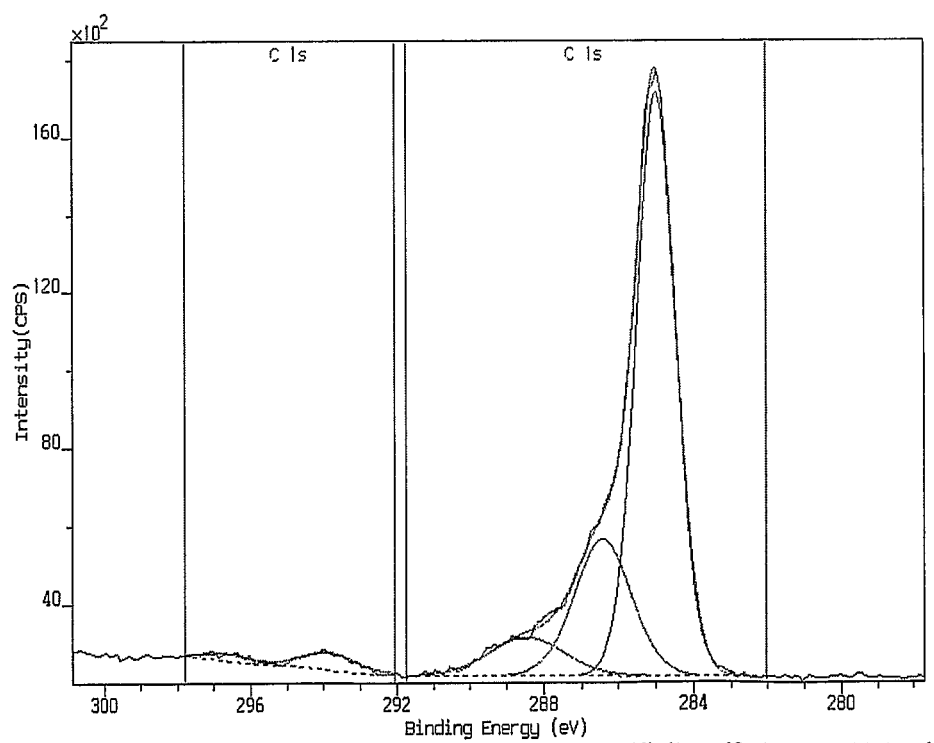

FIG. 13/2
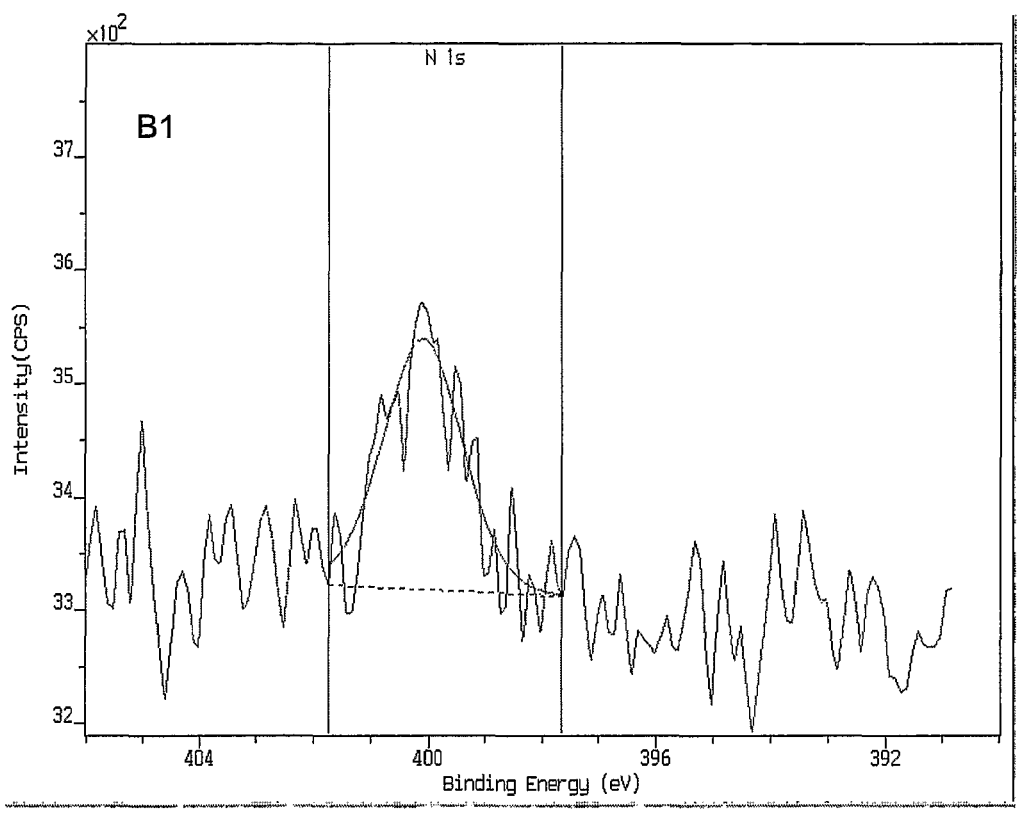
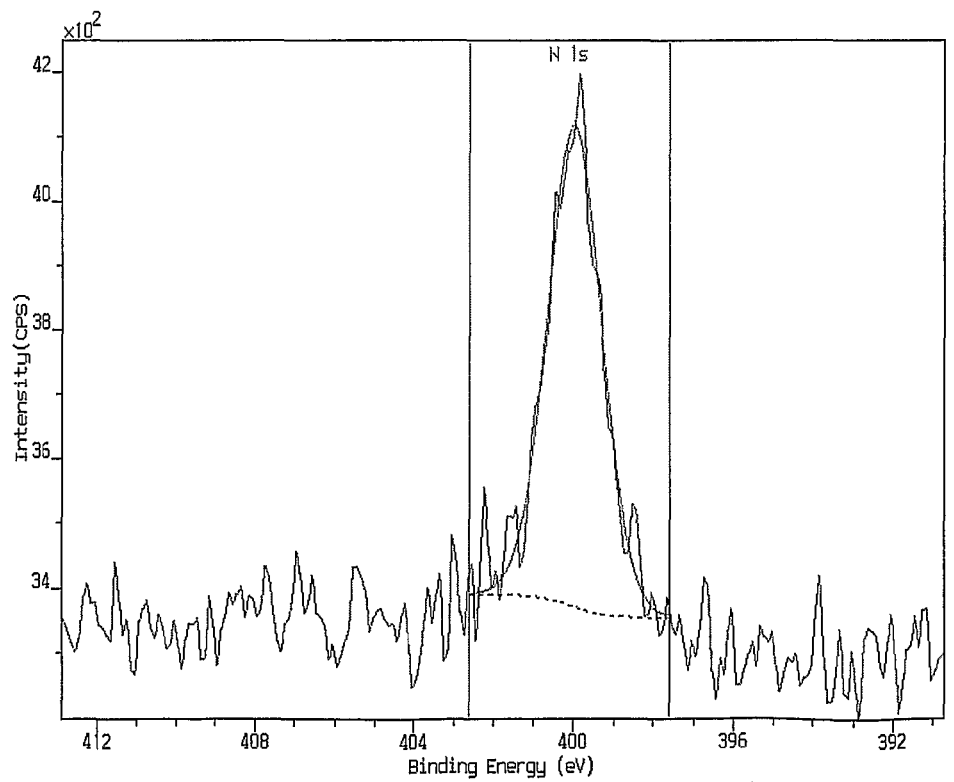

FIG. 13/3
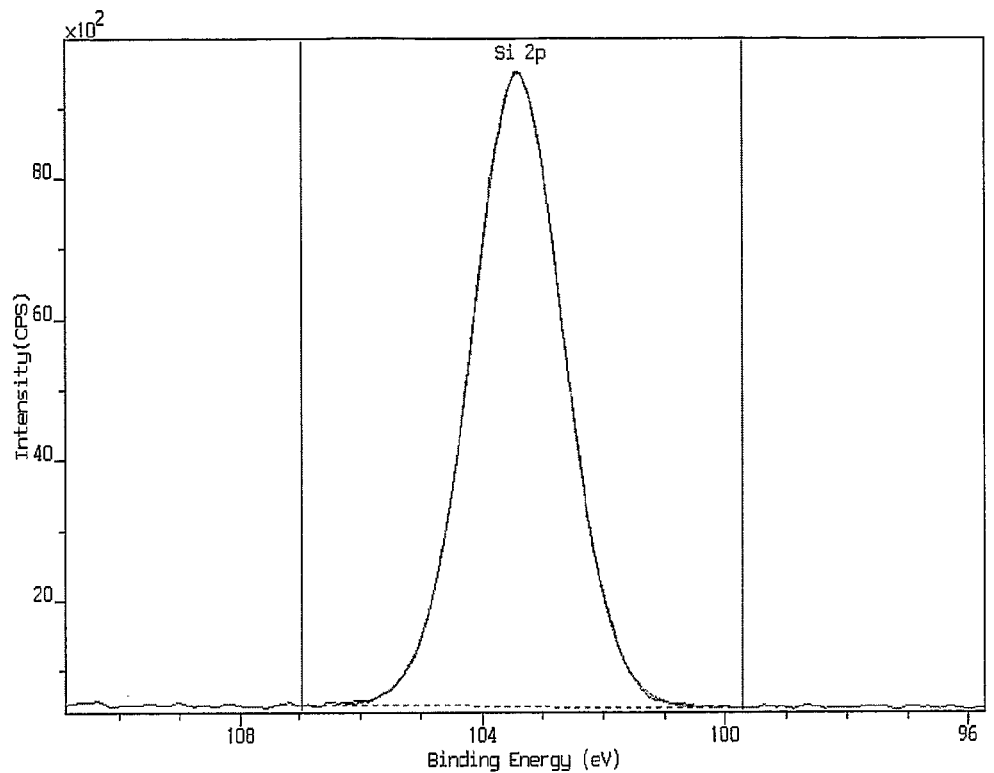
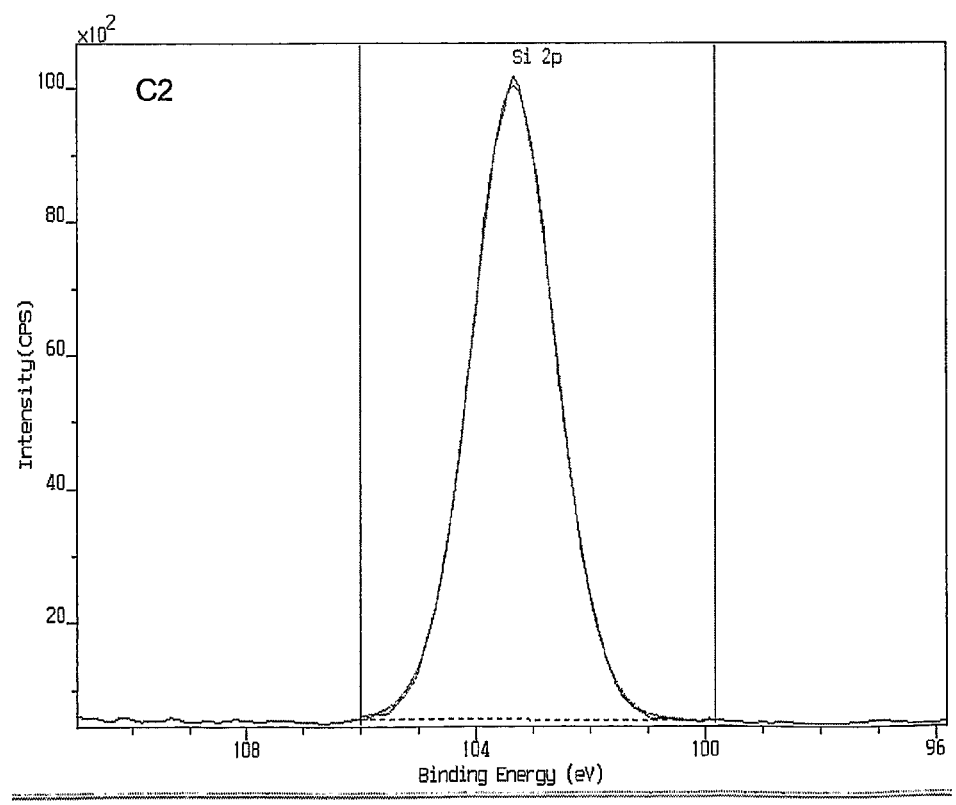

ONLINE CONTAMINANT DETECTION AND REMOVAL SYSTEM

CROSS-REFERENCE TO RELATED APPLICATIONS

This application is a filing under 35 U.S.C. §371 of PCT/SG2008/000156 filed under the PCT on May 2, 2008, and claims the benefit of priority of US provisional application No. 60/915,718 filed May 3, 2007, by Karina Yew-Hoong Gin and Trevor R. Garrett, the contents of each being hereby incorporated by referenced in its entirety for all purposes.

FIELD OF THE INVENTION

The present invention refers to continuous flow devices suitable for immediate detecting and/or removing of contaminants from a liquid stream of processed water and methods using these devices.

BACKGROUND OF THE INVENTION

Water purification processes and potable water standards are improving all the time. However, in light of today's new water processing techniques and the knowledge of toxins, viruses, microorganisms, in particular contaminants of the aforementioned groups which are pathogenic for humans, and their ability to diversify, water processes and lines need to be monitored stringently. A lapse in the purification process or water pipe infrastructure could cause a significant spread of disease. With the projected increases for demand in water requirements, online monitoring systems for such contaminant are becoming more necessary.

For example, at present, microbiological quality control of the treated water is time consuming and inefficient. Like the chemical monitors in industry, pathogen monitors should respond on contamination, effecting an instant stop of the water purifying process on detection of contaminants. This will reduce the likelihood of any contaminant being transferred into the public domain.

Thus, it is important to assure that the water supplied to the general public by water utility boards is free of contaminants 24 hours a day. However, until today the time between sampling and response to a positive result (24 hours) is normally not sufficient to prevent contaminated water from reaching the public.

Different methods are used to detect contaminants. Detection of contaminants normally requires two general steps. The first step is the target capture, in which the contaminant of interest is removed, tagged or amplified to differentiate it from the remaining material in the sample. This step is typically responsible for the selectivity of the approach. The second step is the detection, in which the captured, tagged or amplified contaminant is counted or measured quantitatively. The detector typically acts as a transducer, translating the biological, physical, or chemical alteration into a measurable signal. In most cases where microorganism are to be detected, a third step, preconcentration, may be added prior to target capture because most liquids to be analyzed have relatively dilute levels of microorganism compared to other applications. For example, recreational water standards for bacterial indicators are roughly 100 cfu/100 ml, or 1 cell/ml. Since many detection methods are based on measuring less than a single cell, preconcentration may be necessary to achieve acceptable precision.

There are three broad classes of capture methods used in rapid detection technology which can be summarized as follows (Noble, R. T. and Weisberg, B.; 2005; Journal of Water and Health; vol. 03.4; p. 381). Firstly, molecular whole-cell and surface recognition methods capture and/or label the target compound by binding to molecular structures on the exterior surface or to structures within the interior of, a microorganism, virus, or to genetic material of interest. These include depending on the compound to be detected immunoassay techniques, bacteriophage, and molecule-specific probes, such as lipid or protein attachment-based approaches. Secondly, nucleic acid detection methods target specific nucleic acid sequences of bacteria, viruses, spores of bacteria or protozoa. These include polymerase chain reaction (PCR), reverse transcriptase polymerase chain reaction (RT-PCR), quantitative PCR (Q-PCR), nucleic acid sequence based amplification (NASBA), and microarrays. Thirdly, enzyme/substrate methods are based upon either existing chromogenic or fluorogenic substrate methods already in wide use, or new enzyme-substrate approaches. Enzyme/substrate methods are enhancements of currently approved methods such as the defined substrate technology employed in the commercial kits, Colilert® and Enterolert® (IDEXX Laboratories, Inc).

IDEXX kits are US EPA-approved tests, and are subsequently used as the standard water quality monitor for bacteria. The kits are cheap, reliable, sensitive, widely used, easily used and require little preparation of samples.

A disadvantage of the IDEXX kit as well as of most other methods referred to above is that it takes a long time to acquire results due to necessary sample/kit incubation periods. For example, the IDEXX kit takes between 18 hours to 25 hours to acquire results after sampling. This significant limitation prevents, for example, the use of this technique for rapid online applications. However, any new technology would need to be compared to IDEXX techniques owing to the fact that it is the technology currently employed as a standard internationally.

Different detection methods have different problems. For example, PCR technology and micro-arrays require the water samples taken to be treated with tedious enrichment and DNA extraction procedures, making exploitation of these techniques for online applications very difficult. Bacteria in environmental waters have also been monitored using flow cytometric techniques. In this case enrichment and cell preparations are usually necessary due to the low levels of poorly differentiated organisms normally present in such samples. Micro-fluidics as the name suggests are used to analyze small liquid volumes, when considering the large volumes of water purified in water processing plants this technique is obviously limited.

Thus, there is a high demand for detection methods which allow a sensitive but at the same time fast detection of contaminants.

SUMMARY OF THE INVENTION

In a first aspect, the present invention refers to a continuous flow device suitable for detecting and/or removing of at least one contaminant in a liquid stream, comprising:
  a) at least one cartridge wherein the circumferential wall of the cartridge comprises a first inlet and a first outlet for the liquid stream and further comprises a radiation incident wall portion and a radiation emerging wall portion; wherein the cartridge further comprises optically transparent support material;
    wherein the optically transparent support material is packed in the cartridge such that a liquid stream can pass between voids or spaces formed within and/or by the optically transparent support material;

wherein the optically transparent support material comprises molecules for capturing the at least one contaminant,
wherein the capture molecules are immobilized on the surface of the support material;
wherein each of the capture molecules further comprises at least one reporter group which emits a signal upon binding of the at least one contaminant;
b) at least one radiation source for emitting a radiation beam for excitation of the reporter group;
c) at least one detector for detecting the signal emitted by the at least one reporter group.

In another aspect, the invention refers to a continuous flow device suitable for detecting and/or removing of at least one contaminant in a liquid stream, comprising:
a) at least one rotatable support positioned within the liquid stream comprising molecules for capturing the at least one contaminant wherein the capture molecules are immobilized on the surface of the rotatable support;
wherein each of the capture molecules further comprises at least one reporter group which emits a signal upon binding of the at least one contaminant;
b) at least one radiation source emitting a radiation beam for excitation of the at least one reporter group;
c) at least one detector for detecting the signal emitted by the at least one reporter group.

In another aspect, the present invention refers to a continuous flow method suitable for detecting and/or removing of at least one contaminant from a liquid stream using a device according to the present invention, wherein the method comprises directing a liquid stream along or through the device.

In still another aspect, the present invention refers to the use of a device according to the present invention or to a method according to the present invention for online detecting and/or removing of contaminants from a liquid stream.

In a further aspect, the present invention refers to a cartridge adapted to be used in a continuous flow device suitable for detecting and/or removing of at least one contaminant in a liquid stream, wherein the cartridge comprises:
a circumferential wall having a first inlet and a first outlet for the liquid stream and a radiation incident wall portion and a radiation emerging wall portion;
wherein the cartridge further comprises optically transparent support material;
wherein the optically transparent support material is packed in the cartridge such that a liquid stream can pass between voids formed within and/or by the optically transparent support material;
wherein the optically transparent support material comprises molecules for capturing at least one contaminant, wherein the capture molecules are immobilized on the surface of the material;
wherein each of the capture molecules further comprises at least one reporter group which emits a signal upon binding of the at least one contaminant.

In another aspect, the present invention also refers to rotatable support adapted to be used in a continuous flow device suitable for detecting and/or removing of at least one contaminant in a liquid stream, wherein the rotatable support comprises molecules for capturing at least one contaminant wherein the capture molecules are immobilized on the surface of the rotatable support; and wherein each of the capture molecules further comprises at least one reporter group which emits a signal upon binding of the at least one contaminant.

BRIEF DESCRIPTION OF THE DRAWINGS

The invention will be better understood with reference to the detailed description when considered in conjunction with the non-limiting examples and the accompanying drawings, in which:

FIGS. 1A and 1B show diagrams illustrating different aspects of the continuous flow device of the present invention. (100) is the circumferential wall of the cartridge while (150) is the radiation incident and (200) the radiation emerging wall portion. In FIG. 1A the position of the radiation emerging wall portion (150) which leads to the detector is opposite to the position of the radiation incident wall portion (200). In FIG. 1B the radiation source and the detector are positioned on the same side of the cartridge so that the radiation emerging wall portion (150) and the radiation incident wall portion (200) fall together. It will be obvious to a person skilled in the art that the position of the radiation source and detector on the one hand and the path of the liquid stream are variable with respect to each other as long as both functions (liquid flow, radiation path) are not disturbed. It should also be noted that the cartridge shown in FIGS. 1A and 1B can also be a rotatable support.

FIG. 3AII also shows an alternative setup for a cartridge, a radiation source and a detector. In this pipe the flow is directed to the periphery of the pipe. This leaves the central lumen vacant for the positioning of a radiation source and detector which revolve on an axis permitting the scan of the support material, such as beads found within the liquid flow portion of the pipe.

FIG. 5 shows the optical section of the device in more detail. In the device illustrated in FIGS. 4 and 5 a radiation source (1) sends radiation of a pre-selected wavelength through lenses (2, 3) which spread the light through the bead cassette (4). The beads (A) have antibodies (B) immobilized onto their surface. Qdots are conjugated to the antibodies which fluoresce at a different wavelength of light when a contaminant such as an microorganism is bound to the immobilized antibodies. This second wavelength is captured by an waveguide such as an optical fibre (5) housed on the adjacent side of the cassette. The wavelength is guided through to a filter (6) and subsequently a photon detector (7). The optical light is then transduced into a digital signal and presented numerically or graphically on computer (8).

In FIG. 6 the rotatable support or rotating head is positioned in a tube through which the liquid steam flows. The rotatable support is connected to a rotating arm which originates from a motor which is connected to a power supply. The motor is fixed by a L-shaped stand. Depending on the consistency of the water flow or the interaction time for binding of the contaminants to the capture molecule immobilized on the rotatable head the revolutions (per minute) of the rotatable support can be increased or decreased.

FIG. 13 (FIGS. 13/1 to 13/3) in connection with Table 1 show the results of the immobilization of the capture molecules on the surface of the support material (in this example glass). The results revealed by the graphs show another illustration of the results shown in Table 1 which summarizes the results obtained with high resolution XPS. High resolution XPS revealed contrasting quantities of carbon, nitrogen and silicone species (found at consistent levels of binding energies (eV)) between the APTS-GA treated and untreated glass surfaces. FIG. 13 reveals the same information as shown in Table 1 in the form of spectra and shows the presence of 3 carbon components: an aliphatic C—C component with a binding energy of 285.0 eV, a C-0 component at 286.5 eV and a C=O component at 288.8. The main peak at 285.0 eV represents aliphatic carbons likely to originate from contaminating carbon sources and from the covalently bonded carbon atoms found within the branch structures of the APTS-GA combination. Functionalisation of the surface by the APTS-GA chemistries sees a total increase in atomic carbon of 8.92%. A tripling of nitrogen species (0.25% to 0.79%) suggests the presence of amino groups after functionalisation. This combined with a slight reduction on the atomic concentration of surface silicone (20.77% to 19.64%) increases the confidence that the glass surface chemistry has been modified appropriately by the functionalisation chemistries. The signal increase of N1s (400 eV) and the C1s peak at (287 eV) suggest that the glass surface has been covalently linked with the APTS-GA.

FIG. 16 2A (black) shows no bacteria present, possibly due to the absence of antibodies. In 2B of the same figure bacteria are clearly exposed by the UV excitation. This is pictorial evidence that the cells are immobilised by the antibodies and also that the UV excitation reveals the cells without the use of a fluorophore. The reason for this lies with the biomolecules contained within the bacteria, in particular the DNA, which is well known to fluoresce under UV conditions (autofluorescence). This can be one of the keys in further reducing costs of the bead cartridge, but also reveals a certain redundancy of the Qdots. This however, does not reduce the usefulness of the qdots (red colored area outside the two white lines) as they can have an accumulating effect on the fluorescence of the bacteria, FIG. 16, 2C (blue fluorescence between the two white lines). A serial dilution of antibodies is used in FIG. 17. Legend to FIG. 17: Glass slides, Epifluorescence Microscopy of *E. coli* K12 immobilised on Qdot (0.002 µM) treated serially diluted antibodies, under blue excitation, ×1000 magnification. A) Antibody concentration of 4.0 mg/ml, B) 0.4 mg/ml, C) 0.04 mg/ml and D) 0.004 mg/ml. Using Qdots (red colored area within the white encircled area) shows that the green fluorescence of the *E. coli* is independent of antibody concentration. Images have been chosen to show fluorescence of the cells as opposed to the immobilising effects of the antibodies. It is also worth noting that after the cells have been exposed to the glass slides, the glass slides have been washed vigorously, suggesting that the bond between the antibodies and the cells is a strong bond.

DETAILED DESCRIPTION OF THE INVENTION

In one aspect, the present invention refers to a continuous flow device suitable for detecting and/or removing of at least one contaminant in a liquid stream, comprising:
  a) at least one cartridge wherein the circumferential wall of the cartridge comprises a first inlet and a first outlet for the liquid stream and further comprises a radiation incident wall portion and a radiation emerging wall portion;
    wherein the cartridge further comprises optically transparent support material;
      wherein the optically transparent support material is packed in the cartridge such that a liquid stream can pass between voids formed within and/or by the optically transparent support material;
      wherein the optically transparent support material comprises molecules for capturing the at least one contaminant,
      wherein the capture molecules are immobilized on the surface of the material;
      wherein each of the capture molecules further comprises at least one reporter group which emits a signal upon binding of the at least one contaminant;
  b) at least one radiation source for emitting a radiation beam for excitation of the reporter group;
  c) at least one detector for detecting the signal emitted by the at least one reporter group.

This device allows reducing the response time of contaminant analysis to seconds instead of hours to days like in conventional detection devices or methods referred to in the introductory part of the application. This short response time allows decreasing the probability of infection, reduces overhead costs and provides for a 24 hour monitoring for all point sources considered key. Therefore, this system encourages a review of current quality legislation for example for municipal drinking water or other types of processed water. Due to its unique construction it is possible to monitor a continuous flow of a liquid stream instead of taking samples which need to be analyzed separately. A detection of contaminants effects then an instant stop of the connected cycle of a liquid stream.

The cartridge comprising the capture molecules also allows enrichment of contaminants even if their concentration in the liquid stream is very low, thus making any following pre-incubation step(s) for enrichment needless. At the same time, the capture molecules in the cartridge also allow removal or at least a substantial reduction of the amount of contaminants in the liquid stream.

Figure 4:
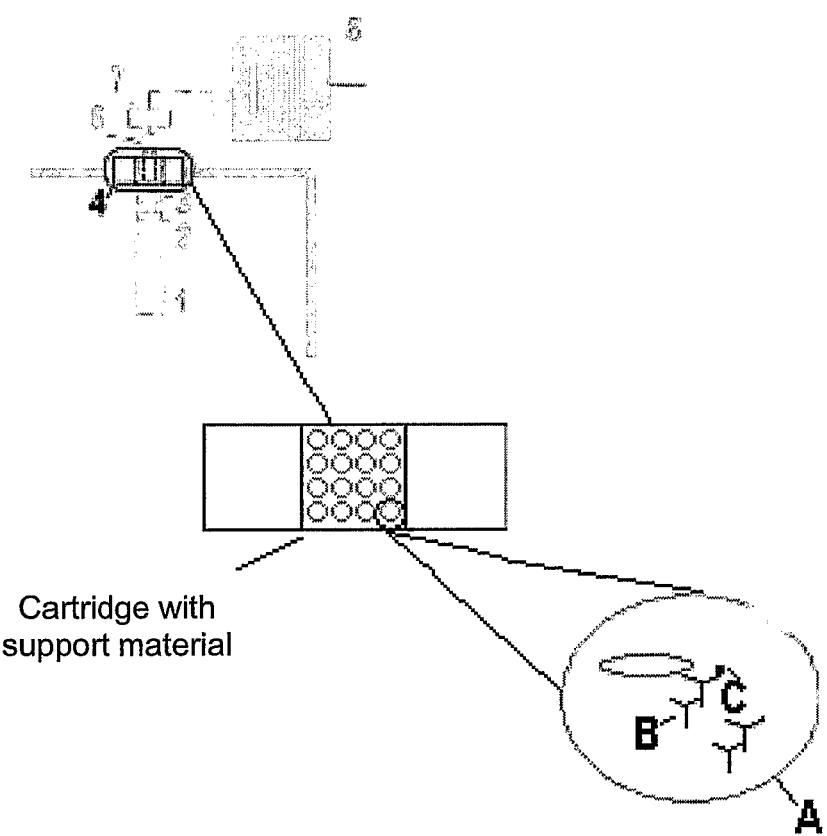
FIGS. 4 and 5 show another configuration of a continuous flow device of the present invention in different perspectives.
Figure 5:
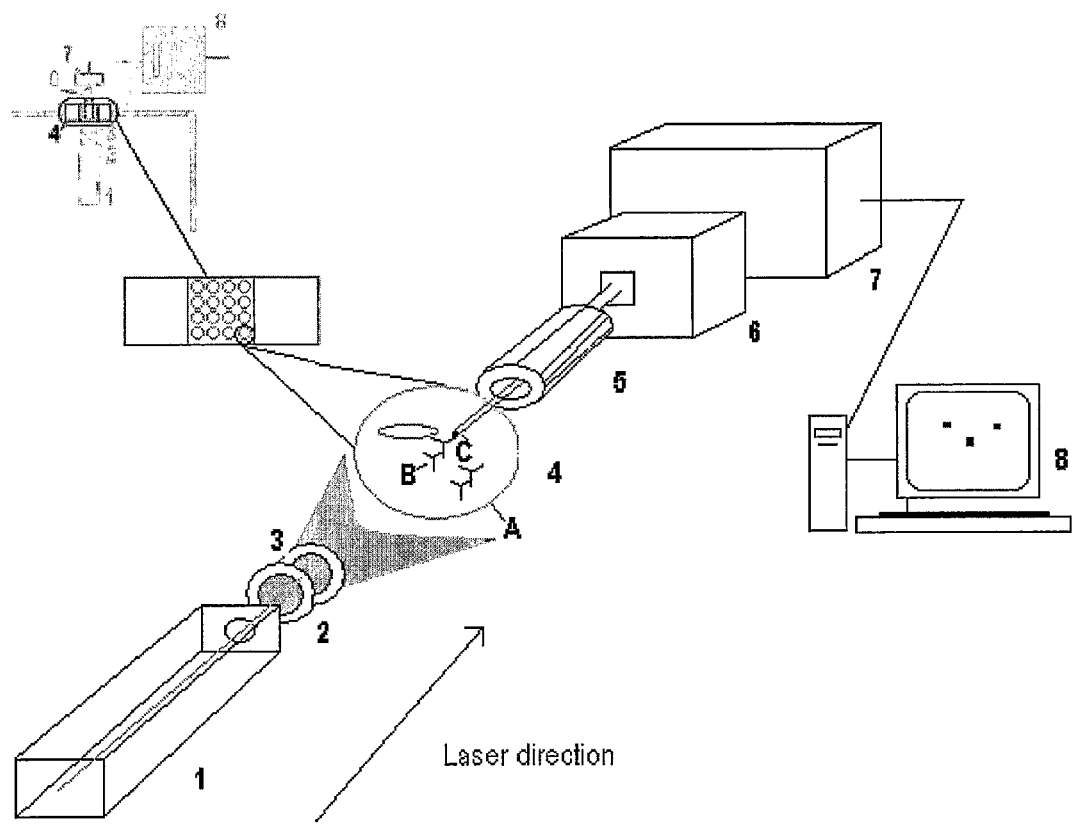

The core element of this device is the cartridge or bead cassette as illustrated in more detail, for example, in FIGS. 4 and 5. The cartridge comprises an optically transparent support material "matrix" constituted of the beads, the labeled capture molecules and any other molecule immobilized thereon. A sensitive signal detector is positioned strategically so that any signal send from the matrix is captured immediately. This reduces the current lag phase of the systems used in the art between sample collection and data acquisition significantly.

The cartridge serves three different purposes. Firstly, the cartridge traps contaminants contained in the liquid stream flowing through the cartridge (enrichment of contaminants). Secondly, the mechanism used to trap or catch the contaminants in the cartridge via the capture molecules simultaneously provides the mechanism of signaling on contaminant attachment to the capture molecules (sample preparation). The sensitive signal detector is positioned strategically so that any signal sent from the matrix comprising the capture molecule binding the contaminant is captured immediately (microorganism detection). The specificity of the capture molecule further enables to identify the organisms trapped in the matrix directly.

Figure 2:
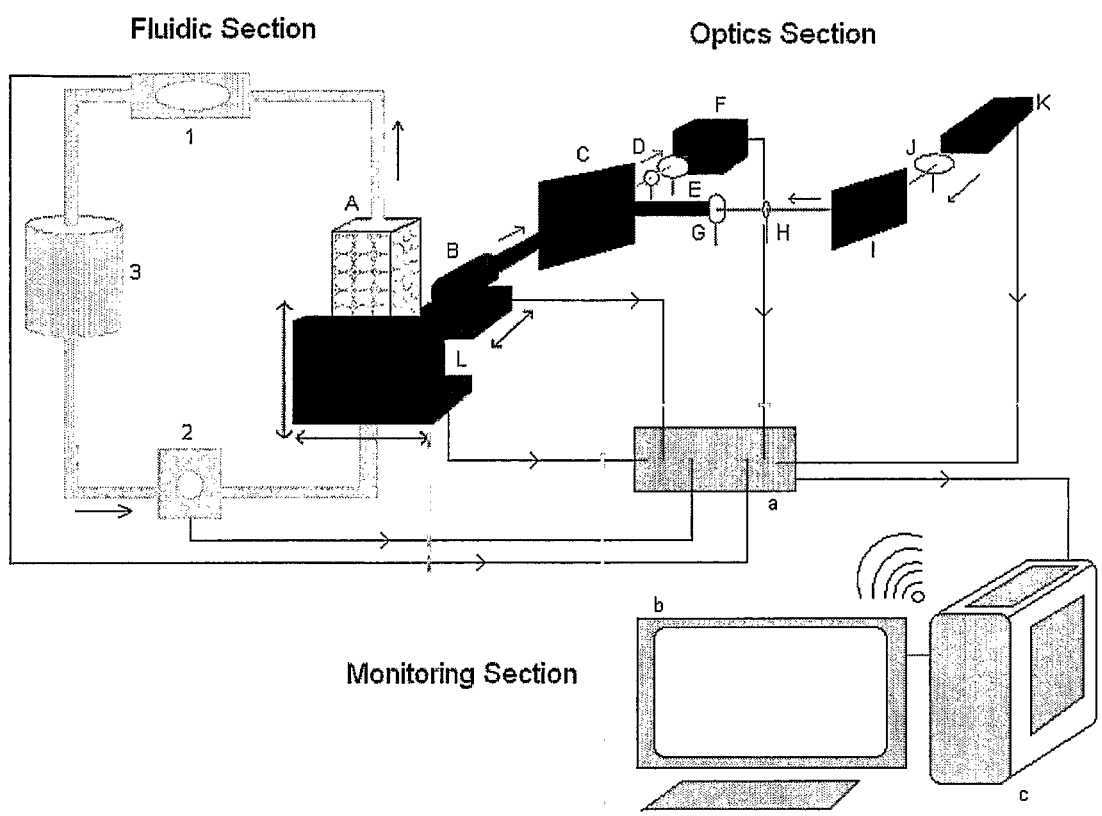
FIG. 2 shows an exemplary setup of a device of the present invention using a cartridge filled with beads used as optically transparent support material. This system includes some additional parts like the flow measuring device (1), a pump (2) and the reactor vessel (3) which have been used only for characterizing and optimizing of the system of the present invention during its development phase. In this Figure the cartridge is placed on a linear translation stage (L) attached to the objective lens (B) through which the excitation radiation/light is directed into the cartridge. The translation stage (L) allows movement of the cartridge in front of the objective lens (B) in order to scan the entire cartridge with the laser. The objective lens (B) also serves to capture the light emitted by the reporter groups upon binding of a contaminant. The light emitted by the reporter groups being of another wavelength than the excitation light and only the light emitted by the reporter groups passes through the dichroic mirror (C) and reaches the detector (F).

As can be seen in FIG. 2, the cartridge is incorporated in a fluidic section, an optic section as well as to a monitoring section. The liquid stream to be screened for contaminants passes through a first inlet into the cartridge and exits the cartridge through the outlet. FIGS. 3AI, 3AII to 3C illustrate different exemplary configurations of a cartridge having an inlet and an outlet in different positions of the cartridge. In general, the inlet and the outlet can be located at any desired position relative to a selected point or region of the cartridge. In FIG. 3AI, the liquid stream enters the cartridge through an inlet located at the bottom corner and passes the beads through to an outlet located at the opposite top corner of the cartridge. It should be noted that besides the specific location of the inlet and outlet for the liquid stream illustrated in FIG. 3AI other possibilities of arranging the inlet and outlet in a shifted manner are possible.

For example, starting from FIG. 3AI it is also possible to have more than one inlet and/or more than one outlet. When looking at FIG. 3AI it is for example possible that two inlets are located at different positions at the bottom side of the cartridge (for example at the outer ends of the bottom side of the cartridge) and one outlet is positioned in the center of the cartridge at the top side as illustrated in the small encircled picture next to FIG. 3AI.

It is further always possible to redirect the direction of the flow through the cartridge because the flow direction will not influence the detection of the signals emitted by the reporter groups connected to the capture molecule which has bound the contaminant to be detected.

Examples of an inlet include, but are not limited to, a valve, a chamber, a neck or a channel. In some examples the inlet is an opening. A respective opening may be of any shape, profile and diameter.

In another aspect illustrated in FIG. 3AII the detector is located in a central pipe surrounded by an outer pipe through which the liquid stream flows. The inner wall of the outer pipe includes the incident wall portion as well as the emerging wall portion, i.e. the position of those two portions is congruent. In this pipe the flow is directed to the periphery of the pipe. This leaves the central lumen vacant for the positioning of a detector, such as a CCD camera, which revolve on an axis permitting the scan of the beads found within the liquid flow portion of the pipe.

Figure 3B:
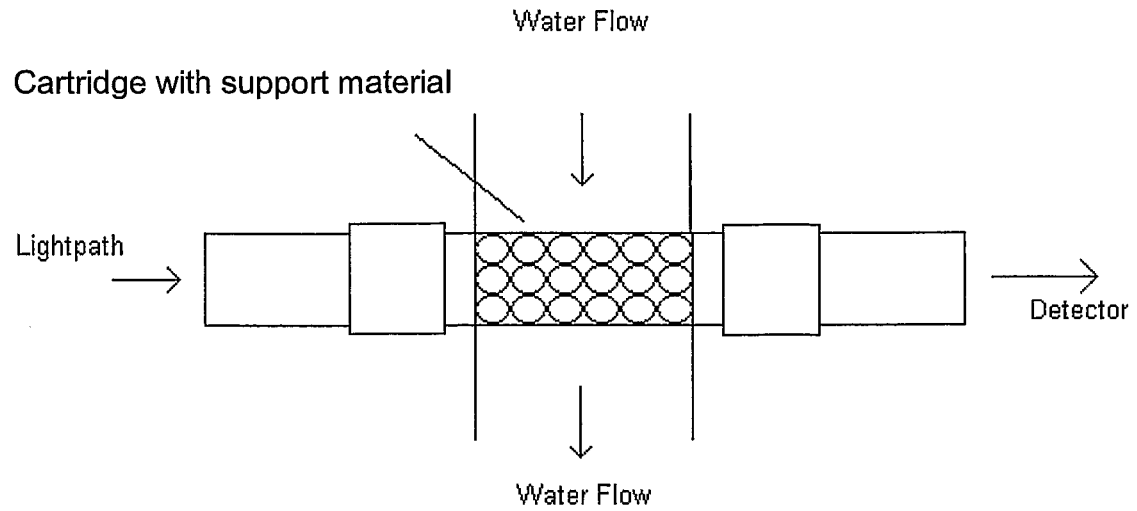
FIGS. 3AI, 3AII to 3C show different configurations of the inlets and outlets of the cartridge. In addition.
FIG. 3C shows how a cartridge can be placed in a pipe to avoid formation of bubbles.
Figure 3C:
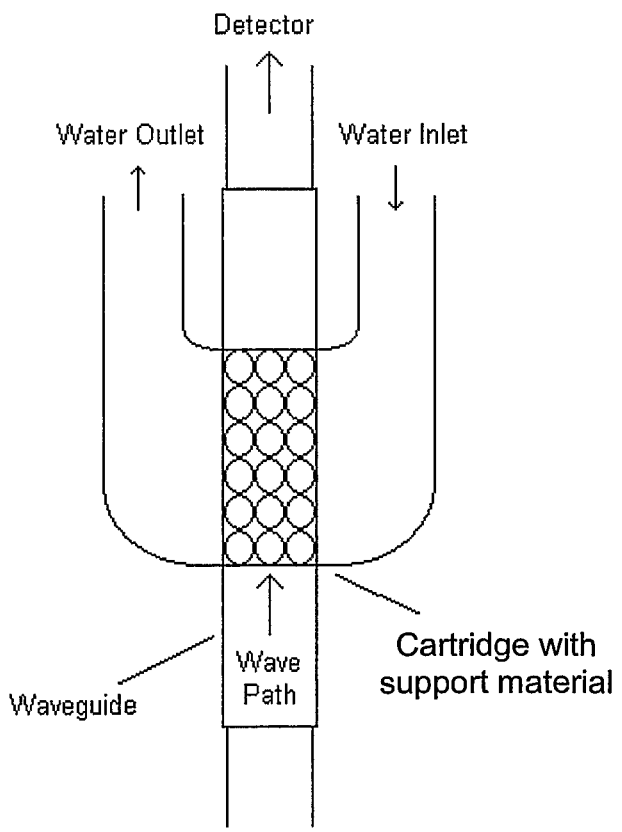

In other configurations illustrated in FIGS. 3B and 3C, the liquid stream can enter and exit the cartridge over the whole length of one side of the cartridge. In FIG. 3C the cartridge is furthermore located at the bottom of a U-shaped pipe feeding the cartridge with the liquid stream. The U-shaped pipe serves the purpose of eliminating the possibility that air bubbles pass through the cartridge.

Considering the flow of the liquid stream through the cartridge, such as the cartridges illustrated in FIGS. 3AI, 3B and 3C, it is obvious that the material of the circumferential wall of the cartridge needs to be composed in a way which allows retaining the optically transparent support material within the cartridge and at the same time allows the liquid stream to enter and exit the cartridge. Thus, the inlets and outlets can comprise an orifice or opening which is spanned by a water permeable membrane or a mesh network dense enough to retain the support material within the cartridge but wide enough to allow a free flow of the liquid stream through the cartridge or bead cassette. Such a membrane or mesh network can have the additional effect of retaining any larger particles which might still be contained in the liquid stream from entering the cartridge thus avoiding clogging of the cartridge.

The pore size of such a membrane or mesh network (e.g. a wire mesh or a mesh network made of poly(tetrafluoroethylene) (PTFE)) depends on the size of the support material within the cartridge. The pore size should at least be smaller than the diameter of the support material. Another alternative is to have a cartridge entrance that is smaller than the support material, such as beads, themselves.

FIGS. 3A to 3C also indicate the incident wall portion and the emerging wall portion. The radiation coming from the radiation source enters the cartridge through the incident wall portion and exits the cartridge through the emerging wall portion. The signal from the reporter group exits the cartridge also through the emerging wall portion to be captured by the detector. In FIGS. 3AI, 3B and 3C the light emerging wall portion is opposite to the light incident wall portion. However, in one example it is also possible that the position of the incident wall portion and the emerging wall portion are congruent, i.e. there is only one wall portion through which radiation enters as well as exits the cartridge (see FIG. 3AII). In another example, more than one emerging and/or incident wall portion exists. In such a case radiation can enter and exit the cartridge through more than one wall portion. In such a configuration it can also be possible that there are two wall portions of the cartridge which both allow radiation to enter as well as exit the cartridge.

In case the position of the incident wall portion and the emerging wall portion are congruent, the wall portion on the opposite site of the incident wall portion and the emerging wall portion can be coated with a reflective material to allow any light not going into the direction of the incident and emerging wall portion to be reflected so that it is redirected towards the incident and emerging wall portion, i.e. the wall portion which leads to the detector. It is also possible that not only the opposite site of the incident wall portion is coated with a reflective material but in general the whole circumferential wall of the cartridge which is not part of any opening or exit. Instead of coating the opposite wall with a reflective material it would also be possible to place a reflective separate wall, such as a mirror, behind the opposite wall portion outside the cartridge. The mirror can also fulfil the same task and redirect any light leaving the cartridge at another position than through the emerging wall portion so that the light is redirected back into the cartridge towards the emerging wall portion.

Examples of reflective materials include but are not limited to front/back surface mirrors, aluminium, gold, silver, band pass, Ar-Ion mirrors, foils and coatings. They can be used as reflective materials for the containment of fluorescent light emitted from the contaminants and reporter groups not initially directed towards the objective leading to the detector.

The material the circumferential wall of the cartridge is made of allows radiation to pass through the incident wall portion and the emerging wall portion. Other parts of the outside of the circumferential wall can be made of an opaque material in order to avoid that any scattered radiation from outside the cartridge disturbs the measurement of the radiation emitted by the reporter groups. To prevent any light from entering the cartridge (i.e. flow cell) material such as a black aluminium foil with a matte finish can be used to adsorb any reflective light from ambient or conventional light sources. Black flocked self-adhesive paper can also be used. Black flocked self-adhesive paper is a very black adhesive material made of many fine fibres which adsorbs almost 100% of the light that strikes it and works as a very effective light trap material.

However, for some commercial applications it can be more economic to manufacture the cartridge only out of one material, i.e. a optically transparent material and place the cartridge later on in another container being made of an opaque material having openings or recesses for the inlet, outlet, the incident wall portion and the emerging wall portion. Instead of placing the cartridge in another container it is also possible to subsequently coat the outside of the cartridge with an opaque material or paint as for example the materials described above.

At least the portions of the circumferential wall of the cartridge through which the radiation enters or the whole cartridge are made of a material which allows radiation to pass through. Examples, for such materials include, but are not limited to, glass, quartz and plastic material. Suitable plastic materials for the construction of the radiation incident wall portion and the radiation emerging wall portion include, but are not limited to, acrylic plastics, such as polymethylmeacrylates (e.g. polymethyl-methacrylate (PMMA), carbazole based methacrylates and dimethacrylates); polystyrene, polycarbonate, polycyclic olefins and optical negative index metamaterials. Elements used to fabricate metamaterial include, but are not limited to silver and gold (Shalaev V. M., 2007, Nature photonics, vol. 1, p. 41). A further illustrative example of a material that is additionally suitable for the generation of a wall portion that allows radiation to pass only to a certain extent is fluoro-ethylen-propylen (FEP). The material of the radiation incident wall portion and the radiation emerging wall portion may be selected independent from one another. In one example the material of the radiation incident wall portion and the radiation emerging wall portion is identical.

The term "radiation" is understood to include electromagnetic radiation of any wavelength, including a distinct wavelength, a set of distinct wavelengths or any region of the electromagnetic spectrum. Two examples of a region of the electromagnetic spectrum are visible light, corresponding to a wavelength range of about 400 to about 700 nanometer, ultraviolet light, corresponding to a wavelength range of about 30 to about 400 nanometer, and infrared light, corresponding to a wavelength range of about 700 nm to about 1 mm. Accordingly the cartridge includes at least two wall portions that allow radiation to enter into and emerge from the cartridge. The radiation is emitted either by a laser or by a photodiode.

For example, when quantum dots or fluorophores are used, the out put power and the wavelength, e.g. 355 (near UV), are important characteristics of a laser as this provides the excitation energy. The output power can be about 1 to 10 mW, 1 to 50 mW or about 500 to 1000 mW. Insufficient energy will not provide sufficient excitation. Also, the pulse operation of a laser allows determining fluorescent life times, as well as fluorescent intensity. A laser can have single pulse energy from about 0.1 µJ to about 10 µJ. The pulse duration can be between about 10 ns to about 15 ns. Fluorescent life times are correlated to wavelength of emission and can be used as a means for, e.g., cell identification.

An example for a laser that can be used in connection with the present invention is the "DPSS 355 nm UV Laser Module" from Shanghai Dream Lasers Technology Co., Ltd. Which wavelength is selected depends on the reporter groups used because different reporter groups require different wavelength at which they are excited to emit a fluorescence or phosphorescence signal.

In some cases the radiation incident wall portion only allows radiation of a certain wavelength, or certain wavelengths, to enter the cartridge. Furthermore, in some cases the radiation incident wall portion also allows, at least to a certain extent, radiation of a certain wavelength, or certain wavelengths, to emerge from the sample compartment. This can for example be the case when the position of the radiation incident wall portion and the radiation emerging wall portion are congruent. In some examples the wavelength, or wavelengths of radiation that can pass the radiation incident wall portion, and the wavelength, or wavelengths of radiation that can pass the radiation incident wall portion are identical or different. In general the radiation incident wall portion allows the excitation radiation to enter the cartridge whereas the radiation emerging wall portion allows the radiation emitted from the reporter groups to exit the cartridge.

The size and the shape of the cartridge depend mainly on two factors. The first factor would be the size and the shape of the pipe or tube for the liquid stream because the at least one cartridge will be placed within the liquid stream and thus need to fit to the size and shape of the pipe. The second factor depends on the kind of radiation source and detector which is used to measure the signals coming out of the cartridge because the radiation source needs to be able to excitate also the reporter groups located at the opposite site of the incident wall portion through which the excitation radiation enters the cartridge and the detector need to be able to receive the signal from those reporter groups which therefore need to be able to exit the cartridge through the emerging wall portion.

Figure 20:
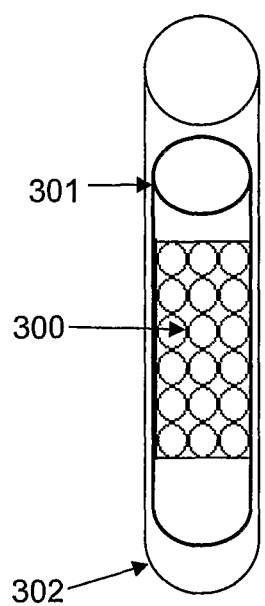
FIG. 20 shows the geometry of a rectangular container comprising the support material (300) which forms the inner compartment of a cartridge (301) wherein the outer shape of the cartridge differs from the shape of the inner compartment to fit into the round tube (302) in which the cartridge is positioned.

In principal, the circumferential wall defining the shape of the cartridge can be of any geometry and dimension. The wall can for instance be curved, round, straight or flat. The geometry of the outer shape of a cartridge can differ from the geometry of an additional inner compartment of the cartridge. If such an additional inner compartment is provided, this compartment does then comprise the matrix with the optically transparent material. For example, the inner compartment has a rectangular shape while the circumferential wall of the cartridge is slightly curved to fit into the water pipe in which the cartridge is placed. Thus, the shape of the inner wall of the cartridge can be different from the shape of the wall forming the outside wall of the cartridge. An example of a cartridge having an inner compartment defined by an inner wall and an outer compartment defined by an outer wall is shown in FIG. 20. The outer wall has a shape which fits the shape of a pipe in which this cartridge is intended to be placed.

The wall of the cartridge can have any thickness as long as it allows passing of the excitation radiation and the radiation emitted by the reporter groups.

In one example, the cartridge has a dimension of about 2.5 cm (width)×1 cm (length)×1 cm (depth). It is also possible to place several cartridges within a pipe or tube or to place more than one cartridge next to each other within a pipe which will allow extending the diameter of a pipe. For example, in case two cartridges having the above dimension are placed next to each other within a pipe, the pipe diameter can be about 5 cm. Furthermore, stronger radiation sources with a longer working distance allow increasing the dimension of the cartridge. It is also possible to use several radiation sources and/or detectors. The cartridge does not need to have a rectangular shape as can be seen from FIG. 3AII. In this embodiment the radiation source and detector are forming a single device which is rotating within the inner lumen of the pipe.

As mentioned before, it is necessary that the excitation radiation can reach every reporter group in the cartridge. Therefore, the cartridge and the radiation source can be movable with respect to each other. That means that either the cartridge is movable in front of the radiation source, or that the radiation source is movable in front of the cartridge or both. As moving the water pipe might be more difficult to realize, it is normally the radiation source which is movable. This also means that the incident and or emerging wall portion need to be adapted in size and shape to allow the radiation to enter and exit over the whole length of the cartridge the laser is passing over. An example of such a configuration is illustrated in FIG. 2. In FIG. 2 the cartridge is positioned on a translatable table which is moved in front of the radiation source which at the same time acts also as detector.

The optically transparent support material is packed in the cartridge so that a liquid stream can pass between the voids formed within and/or by this support material. In addition to forming voids, cavities or free spaces between the support material the support material also carries the capture molecules or other molecules which are all immobilized on the support material. In order to allow the formation of voids the support material need to have an irregular shape, i.e. not a rectangular or square. That means a shape which does not allow that the single particles of the support material are joined smoothly together over the entire length of all of their sides, like bricks in a wall. Thus, the optically transparent support material has a rounded down shape, such as an ellipsoid or spherical shape or mixtures thereof. For example, using spherical particles or beads for the optically transparent support material results in the formation of voids between the beads through which the liquid stream can pass as illustrated for example in FIG. 4.

The optically transparent support material is normally not porous because even though this would enlarge the surface for immobilization of the capture molecules, a porous structure normally leads to multiple refractions which results in the porous material appearing opaque. However, porous support material which is optically transparent can be used in the present invention. "Optically transparent" means that the support material allows the excitation radiation from the radiation source and the emitted radiation from the reporter groups to freely pass through the support material. Otherwise, reporter groups at the opposite end of the incident cartridge wall can not be excited by radiation entering the cartridge. Thus, optically transparent means that the radiation entering the cartridge and created within the cartridge must be able to freely pass the cartridge without being absorbed by the optically transparent support material.

The optically transparent support material can thus be the same as the material listed above for the cartridge wall. In one example, glass beads made of borosilicate are used. In practice the cartridge material and the material of the support material are the same or different with respect to the specific application. Superparamagnetic beads are in general not usable for the purpose of the present invention.

The size of the optically transparent support material packed in the cartridge lies in the macro range which means that the support material has a diameter (measured at the broadest point of the support material) between about 1 mm to about 3 cm or 5 mm to about 2 cm. In general the support material can also have a dimension going up into the meter scale. In one example, support material having a diameter of about 6 mm is used.

Turning now to the capture molecules and the reporter groups, the following passages will describe the kind of interaction between the surface of the support material and the molecules immobilized thereon. The capture molecule and optionally also other molecules, such as, e.g. enzymes, are immobilized on the surface of the optically transparent support material packed in the cartridge. Due to the fact that the flow rate through the cartridge and the liquid volume passing through the cartridge is much higher in the present invention than in other devices known in the art, e.g. flow cytometry, the link between support material and capture molecule need to be strong to avoid washing out of the capture molecule by the liquids passing through the cartridge.

Before attaching molecules to the surface of the support material it can be beneficial to subject the surface of the support material to a chemical treatment to improve the subsequent binding of molecules to it. Coupling agents are used whenever it is necessary to couple two dissimilar materials with each other. To promote adhesion between inorganic surfaces and polymeric molecules silane coupling agents are used. When using silane coupling agents the process is called "silanisation" which results in the conversion of active silanol (SiOH) groups on surface of (for example) glass into less polar silyl ethers (SiOR), thereby making the surface less adhesive. Coupling agents for this process are known in the art (Plueddemann E. P., Silane coupling Agents, Plenum Press, London, 1991). At one end silane coupling agents have alkoxy silane groups capable of reacting with OH-rich surfaces and at the other end they have a large number of functional groups which can be tailored as a function of the matrix to be used. A general formulation for organofunctional silanes is:

$$R'\text{---}Si\text{---}(OR)_3 \qquad \text{(Formula I)}$$

In which R' is a functional group and R is a hydrolysable alkyl group. According to this structure, two different reactions may take place: the alkoxy group which has been hydrolyzed to silanole reacts with the mineral surface; on the other hand the organofunctional group has the capability to react with an appropriate polymer. Examples of organofunctional groups which can be used are trichlorovinylsilane, triethoxyvinylsilane, 3-glycidoxypropyltrimethoxysilane, 3-aminopropyltrimethoxysilane and [β-(3,4-Epoxycyclohexyl)-ethyl]trimethoxysilane.

Figure 8:
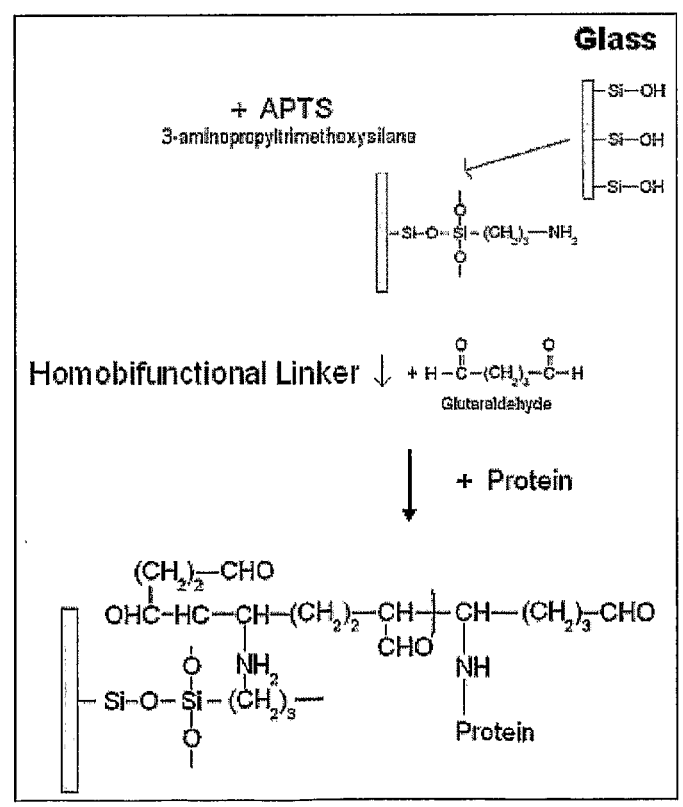
FIG. 8 illustrates an example for the functionalization of the surface of a support or support material. In this case a glass surface is modified to carry a capture molecule (protein). Therefore, the surface is treated with 3-aminopropyltri-methoxysilane ($H_2N-(CH_2)_3-Si-(OC_2H_5)_3$, APTS) to activate the surface to support immobilisation. Subsequently glutaraldehyde ($HCO-(CH_2)_3-COH$) is added which is a homobifunctional linker and which acts as the bridging agent between the solid support and the capture molecule (protein) to be immobilised.

Such coupling agents are capable of covalently attaching the required primary and/or secondary amino groups of a molecule to be attached to the substrate surface. One exemplary way to silanise a silicon surface (see FIG. 8) is to treat the surface with 3-aminopropyltrimethoxysilane ($H_2N$—$(CH_2)_3$—$Si$—$(OC_2H_5)_3$, APTS) to activate the surface to support immobilisation and subsequently glutaraldehyde ($HCO$—$(CH_2)_3$—$COH$) is added which is a homobifunctional linker which acts as the bridging agent between the solid support and the protein to be immobilised. For example, glutaraldehyde on binding with the APTS provides a second amine which can bind covalently to antibodies, protein A or protein G which are presenting carboxyl groups.

Glutaraldehyde is an example for a homobifunctional linker. Homobifunctional crosslinkers have two identical reactive groups and are commonly used in one-step reaction procedures to crosslink proteins to each other or to stabilize quaternary structure. Further examples of homobifunctional crosslinkers are, but are not limited to bis(sulfosuccinimidyl) suberate ($BS^3$), dimethyl adipimidate•2 HCl (DMA), dimethyl pimelimidate•2 HCl (DMP), dimethyl suberimidate•2 HCl (DMS), disuccinimidyl glutarate (DSG), disuccinimidyl tartrate (DST), ethylene glycobis(-succinimidylsuccinate) and dris(succinimidyl) aminotriacetate (TSAT).

In the present invention, heterobifunctional crosslinkers can also be used. Heterobifunctional crosslinkers possess two different reactive groups that allow for sequential (two-stage) conjugations, helping to minimize undesirable polymerization or self-conjugation. Heterobifunctional reagents can be used when modification of amines is problematic. Amines are sometimes present at the active sites of proteins and modification of these may lead to activity loss. Other moieties such as sulfhydryls, carboxyls, phenols and carbohydrates may be more appropriate targets. A two-step strategy allows a protein that can tolerate the modification of its amines to be coupled to a protein or other molecule having different accessible groups. Examples of heterobifunctional crosslinkers are, but are not limited to dicyclohexylcarbodiimide (DCC) and 1-ethyl-3-[3-dimethylaminopropyl]carbodiimide hydrochloride (EDC or EDAC).

Introduction of PEO (polyethylene)/PEG (polyethylene glycol) spacers result in a crosslink that imparts favourable properties of increased solubility and reduced immunogenicity to the crosslinked protein or protein-complex. Those spacers can be introduced in the aforementioned homobifunctional or heterobifunctional crosslinkers. Further homobifunctional and heterobifunctional crosslinkers are available, for example, from Thermo Scientific, Pierce Protein Research Products. Additional homobifunctional disuccinimidyl crosslinkers are also disclosed in U.S. Pat. No. 5,380,873.

Following the pretreatment, if necessary, of the surface of the optically transparent support material the capture molecule will be immobilized on the support material.

Capture molecules which can be used in the present invention include, but are not limited to antibodies, binding fragments of antibodies, aptamers or mixtures of the aforementioned molecules. In another example, the capture molecules include, but are not limited to antibodies, binding fragments of antibodies or mixtures of the aforementioned molecules.

An example of a capture molecule is an immunoglobulin (antibody), a fragment thereof or a proteinaceous binding molecule with immunoglobulin-like functions. Examples of (recombinant) immunoglobulin fragments include, but are not limited to $F_{ab}$ fragments, $F_v$ fragments, single-chain $F_v$ fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). An example of a proteinaceous binding molecule with immunoglobulin-like functions is a mutein based on a polypeptide of the lipocalin family (WO 03/029462, Beste et al., *Proc. Natl. Acad. Sci. USA* (1999) 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see e.g. international patent application WO 96/23879 or Napolitano, E. W., et al., *Chemistry & Biology* (1996) 3, 5, 359-367), proteins based on the ankyrin scaffold (Mosavi, L. K., et al., *Protein Science* (2004) 13, 6, 1435-1448) or crystalline scaffold (e.g. internation patent application WO 01/04144) the proteins described in Skerra, *J. Mol. Recognit.* (2000) 13, 167-187, AdNectins, tetranectins and avimers. Avimers contain so called A-domains that occur as strings of multiple domains in several cell surface receptors (Silverman, J., et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). If desired, a modifying agent may be used that further increases the affinity of the respective capture molecule for any or a certain form, class etc. of analyte molecules.

Antibodies have already been successfully employed for detection of bacterial cells, spores, viruses and toxins alike (Iqbal, S. S., Mayo, M. W., et al., 2000, Biosensors & Bioelectronics, vol. 15, p. 54.9).

For example, in case the contaminants in the liquid stream are bacteria or protozoa monoclonal and/or polyclonal antibodies or any of the immunoglobulin fragments described above can be used. In one example of the present invention rabbit anti *Escherichia coli* (O and K antigenic serotypes) have been used exemplarily.

In order to provide information on the physiological status of cells (bacterial cells, protozoa), or on whether they are living or dead immunoglobulin's can be selected which determine the physiological status of the cell by profiling stage-specific growth proteins on the cell surface (Rompré, A., Servais, P., et al., 2002, Journal of Microbiological Methods, vol. 49, p. 31; Straub, T. M., Chandler, D. P., 2003, Journal of Microbiological Methods, vol. 53, p. 185). For example, differentiation of coliform growth stages can be based on the presence of three cytosolic proteins: DnaK, a metabolically stable protein; Dps, an important protein in stationary-phase or dormant cells which is inversely correlated with growth rate; and F is, which plays a critical role in coordinating rRNA synthesis with growth (Rompré, A., Servais, P., et al., 2002, supra).

Another group of capture molecules that can be used are aptamers. Aptamers are specific RNA or DNA oligonucleotides comprised typically 15-40 nucleotides long or proteins typically comprised of 10 to 20 amino acids which can adopt a vast number of three dimensional shapes. Due to this property, aptamers can be produced to bind tightly to a specific molecular target. Because an extraordinary diversity of molecular shapes exist within all possible nucleotide sequences, aptamers can be obtained for a wide array of molecular targets, including most proteins, carbohydrates, lipids, nucleotides, other small molecules or complex structures such as viruses. Aptamers are generally produced through an in vitro evolutionary process called "systematic evolution of ligands by exponential enrichment" (SELEX). The method is known in the art and is an iterative process based on selection and amplification of the anticipated tight binding aptamer. In addition to high specificity, aptamers have very high affinities to their targets. Typically aptamers generated against proteins have affinities in the picomolar to low nanomolar range (Bunka, D. H. J. and Stockley, P. G., 2006, Nat. Rev. Microbiol., vol. 4 (8), p. 588; Carothers J M, Oestreich S C, et al., 2004, J Am Chem. Soc., vol. 126 (16), p. 5130; Hoppe-Seyler F, Butz K, 2000, J Mol. Med., vol. 78 (8), p. 426).

In order to allow a detection of a signal immediately after binding of a contaminant to a capture molecule, the capture molecule is preferably linked to a reporter group which emits a signal upon binding of the contaminant. The reporter group can be, but is not limited to quantum dots, phosphorescence groups, fluorophore groups, complexes comprising of a fluorophore group and a fluorescence-quenching group or mixtures thereof.

Figure 9:
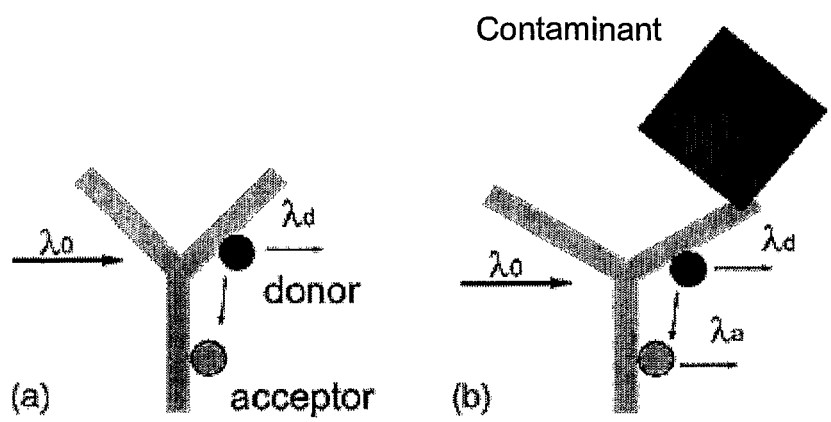
FIG. 9 shows an example of a capture molecule labeled with a reporter group comprising an acceptor-donor fluorophore pair which is emitting a fluorescence signal upon binding of a contaminant. The acceptor fluorophore responds to the excitation form the donor fluorophore only when the distance between them is short enough, e.g. when a contaminant binds to the capture molecule (i.e. antibody in this case). Energy transfer is based on the fluorescence resonance energy transfer (FRET)-based method. $\lambda$ refers to the wavelength emitted by the fluorophore donor ($\lambda_d$) which is emitted upon being excited by the excitation radiation ($\lambda_0$). The radiation emitted by the fluorophore acceptor in response to the radiation from the fluorophore donor is indicated by ($\lambda_a$).

A specific example of a fluorophore group includes, but is not limited to a "FRET acceptor-donor fluorophore pair" which is transferring energy based on the fluorescence resonance energy transfer (FRET)-based method. FRET acceptor-donor fluorophore pairs switch their fluorescence wavelength between donor and acceptor fluorophores as the distance between the two fluorophores change (FIG. 9). Binding those acceptor-donor fluorophore pairs at different positions of the capture molecule leads to an emission of the signal once the contaminant binds to the capture molecule.

FRET acceptor-donor fluorophore pairs are well known in the art (Ko, S., Grant, S. A., 2003, Sensors and Actuators B, vol. 96, p. 372; Oh, B. K., Lee, W., et al., 2005b, Colloids Surfaces a-Physicochem. Eng. Aspects, vol. 257-258, p. 369; Lazcka, O., Del Campo, F. J., Muñoz, F. X., 2007, Biosensors and Bioelectronics, vol. 22, p. 1205) and have been described, for example, in combination with an antibody as capture molecule. As illustrated in FIG. 9 the antibody labeled with such a FRET acceptor-donor fluorophore pair emits a signal upon binding of an antigen, for example a bacterial cell or a protozoa. As a non limiting example the FRET acceptor-donor fluorophore pair Alexa Fluor 546 (FRET donor) and Alexa Fluor 594 is mentioned (purchased from Molecular Probes, Eugene, Oreg.). These FRET acceptor-donor fluorophore pair has already been used for the detection of bacteria of the genus *Salmonella* and *Listeria* (Ko, S., Grant, S. A., 2003, supra). Monoclonal goat immunoglobulin's IgG against *Salmonella* common structure antigens-1 and *Listeria* have been labeled with this fluorophore pair. A person skilled in the art will know that other fluorophore pairs can be used and other capture molecules, such as antibodies, can also be used.

Another class of reporter groups that can be used is quantum dots (Qdots). Quantum dots, also known as nanocrystals, are a special class of materials known as semiconductors, which are crystals composed of periodic groups of II to VI, III to V, or IV to VI materials (IUPAC recommendations of 2006). Quantum dots are unique class of semiconductor having a size ranging from about 2 to 10 nanometer (10 to 50 atoms) in diameter. Because quantum dots' electron energy levels are discrete rather than continuous, the addition or subtraction of just a few atoms to the quantum dot has the effect of altering the boundaries of the bandgap. Changing the geometry of the surface of the quantum dot also changes the bandgap energy, owing to the small size of the dot, and the effects of quantum confinement. The bandgap in a quantum dot will always be energetically larger; therefore, the radiation from quantum dots is referred to be "blue shifted" reflecting the fact that electrons must fall a greater distance in terms of energy and thus produce radiation of a shorter and therefore "bluer" wavelength. The size of the bandgap of quantum dots can be controlled simply by adjusting the size of the dot. Thus, it is possible to tune the bandgap of a dot, and therefore specify its "colour" output depending on the desired application. In other words the colour of light that the quantum dot nanocrystal emits is strongly dependent on the particle size of the quantum dot. Therefore it is possible to control the output wavelength of a dot with extreme precision by adjusting the size of the quantum dot during manufacture. This precise control also allows using different kind of quantum dots emitting different colours and which are connected to different capture molecules directed against different contaminants or targets. Because of this it is possible to include different kind of capture molecules within a cartridge resulting in a cartridge which can detect different contaminants (targets).

Quantum dots are commercially available for example from Invitrogen™ under the name EviTags or EviFluor. They can be used to label all kinds of capture molecules referred to herein. For example, Dwarakanath, S., Bruno, J. G., et al. (2004, Biochemical and Biophysical Research Communications, vol. 325, p. 739) describe the use of quantum dots for labelling antibodies and DNA-aptamers. For example, quantum dots made of semiconductor materials such as CdSe/ZnS can downshift or "blue" shift their fluorescence emission by 60 to 140 nm or more when conjugated to antibodies or aptamers, which are bound to a contaminant, such as a bacterial cell.

Their suitability for the present system relies on the fact that quantum dots offer prolonged fluorescent lifetimes and high quantum efficiencies which is particular important as only a certain percentage of the light emitted by the quantum dots is directed towards the detector, such as a CCD camera with a high sensitivity.

Complexes comprising of a fluorophore group and a fluorescence-quenching group are commonly used for labeling, e.g., aptamers. For example, a fluorophore group and a fluorescence-quenching group are located at the end of a double stranded nucleic acid which is immobilized on the surface of the support material. When hybridized the fluorophore group and a fluorescence-quenching group are located in immediate vicinity to each other which has the effect that now fluorescence can be detected. The hybridized nucleic acid strands are not fully complementary so that hybridization can be disrupted when the target sequence appears which is fully complementary to the nucleic acid sequence of the double stranded nucleic acid. Once the fully complementary target sequence binds the previously hybridized strands separate and the target sequence replaces the previous hybridized strands. This has the effect that the fluorophore group which has previously been quenched by the fluorescence-quenching group can now be detected as it is not any longer located in immediate vicinity to the fluorescence-quenching group.

As becomes obvious from the above description, some reporter groups mentioned herein require to be linked to the capture molecule in order to emit a measurable signal upon binding to the contaminant. Linking of capture molecule and reporter group can be easily achieved using affinity tags known in the art. However, before addressing the different kind of affinity tags it is pointed out to another aspect of the present invention in which in addition or instead of the at least one reporter group a second reporter group is comprised which is located in a microorganism to be detected itself (autofluorescence) and is selected from the group consisting of aromatic amino acids, nucleic acids, disulphide bonds and enzymatic co-factors.

This at least one second reporter group is based on the phenomenon of autofluorescence occurring in all microorganism such as bacteria, protozoa, cyanobacteria and helminths. Microorganisms contain molecules, which become fluorescent when excited by UV/Vis radiation of suitable wavelength. This fluorescence emission, arising from endogenous fluorophores, is an intrinsic property of microorganisms and is called auto-fluorescence to be distinguished from fluorescent signals obtained by adding exogenous reporter groups like the one previously described. Together with aromatic amino acids and lipo-pigments, further endogenous fluorophores are pyridinic (NADPH) and flavin coenzymes. All microorganism contain these biomolecules, for example the amino acids are the building blocks of protein, the nucleic acids are the building blocks of DNA and RNA and the co-factors NAD and NADH are essential for the transport of electrons to the terminal electron acceptor in cellular respiration. In tissues, the extracellular matrix often contributes to the auto-fluorescence emission more than the cellular component, because collagen and elastin have, among the endogenous fluorophores, a relatively high quantum yield. Changes occurring in the cell and tissue state during physiological and/or pathological processes result in modifications of the amount and distribution of endogenous fluorophores and chemical-physical properties of their microenvironment. The advantage of using autofluorescence is that it does not require any treatment of fixing of the microorganism and thus helps to save resources (Monici, M., 2005, Biotechnol Annu Rev., vol. 11, p. 227; Ammor, M. S., Delgado, s., et al., 2007, Journal of Microbiological Methods, vol. 69, p. 100; Ammor, M. S., 2007, J Fluoresc, vol. 17, p. 455).

Each of these autofluorophores has its own excitation and emission spectra and so can be used to discriminate between different microorganism species. Exemplary practical applications of autofluorescence are known in the art. For example, use of autofluorescence is described by Giana, H. E., Jr. Silveira, L., et al. (2003, Journal of Fluorescence, vol. 13, no. 6, p. 489) who identify single species, Wos, M., Pollard, P., (2006, Waterresearch, vol. 40, p. 2084) who determine metabolic activity, Farabegoli, G, Hellinga, C., et al., (2003, Water Research, vol. 37, p. 2732) who study physiological response to environments, and Arunachalam, R. S., Shah, H. K., et al., (2005, Water Research, vol. 39, p. 1205) who monitor aerobic sludge digestion by bacteria.

When using this second reporter-group in addition to the first reporter group which is attached to the capture molecule care should be taken to ensure that the emission wavelength of both reporter groups is different to enable proper identification and to avoid false positive signals.

Affinity tags which are well known in the art can be used to immobilize or link the reporter group to the capture molecule. Tags which can be used include, but are not limited to the different versions of avidin or streptavidin binding tags also including streptavidin muteins, for example those marketed under the trademark STREP-TAG®, and the like. Further examples of streptavidin tags can be found in WO 02/077018, U.S. Pat. No. 6,103,493.

"Streptavidin muteins" are polypeptides which are distinguished from the sequence of wild-type streptavidin (sequence disclosed in Argarana et al., 1986, Nucleic Acids Res. Vol. 14, p. 1871) by one or more amino acid substitutions, deletions or additions and which retain the binding properties of wt-streptavidin. Streptavidin-like polypeptides and streptavidin muteins are polypeptides which essentially are immunologically equivalent to wild-type streptavidin and are in particular capable of binding biotin, biotin derivative or biotin analogues with the same or different affinity as wt-streptavidin. Streptavidin-like polypeptides or streptavidin muteins may contain amino acids which are not part of wild-type streptavidin or they may include only a part of wild-type streptavidin. Streptavidin like polypeptides are also polypeptides which are not identical to wild-type streptavidin, since the host does not have the enzymes which are required in order to transform the host-produced polypeptide into the structure of wild-type streptavidin.

The term streptavidin also includes streptavidin tetramers and streptavidin dimers, in particular streptavidin homotetramers, streptavidin homodimers, streptavidin heterotetramers and streptavidin heterodimers. Each subunit normally has a binding site for biotin or biotin analogues or for streptavidin-binding peptides.

Examples of streptavidins or streptavidin muteins are mentioned, for example, in WO 02/077018, WO 86/02077, DE 19641876A1, U.S. Pat. No. 6,022,951, WO 98/40396 and WO 96/24606. A detailed description of affinity tags in particular streptavidin-biotin can be found in M. Dean Savage, Avidin-Biotin Chemistry: A Handbook, Pierce Chemical Co (January 1992), ISBN 978-0935940114 and Abelson, J. N., Simon, M. I., et al., Avidin-Biotin Technology, Volume 184: Volume 184: Avidin-Biotin Technology (Methods in Enzymology), Academic Press (May 28, 1990), ISBN 978-0121820855.

The different versions of streptavidin bind very strong to biotin or variants of biotin which are also known in the art and are also mentioned in the documents just cited. For example, a capture molecule comprising biotin is binding to streptavidin which is immobilized on the surface of the optically transparent support material. Due to their high binding constant of $10^{-15}$ mol the streptavidin-biotin system is one of the most used systems. Other suitable conjugation systems include, but are not limited to those that bind to amino and carboxyl groups and thiols.

If desired, more than one capture molecule can be immobilised on the surface of the support material. This may for instance be desired in order to broadly screen for the presence of any of a group of selected contaminants. The use of more than one capture molecule can also be desired for the detection of the same contaminant via different regions thereof, e.g. different haptens of a protein or different recognition sequences of a nucleic acid molecule, e.g., the 5'- and 3'-termini thereof, which enhances the likelihood to detect even a few copies of a contaminant (e.g. nucleic acid, bacteria, spores, protozoa etc.) in a liquid stream.

Turning now to the contaminants to be detected, the great diversity of capture molecules which can be immobilized on the surface of the support material allows detection of several different contaminants. Such contaminants can be, but are not limited to viruses, bacteria, cyanobacteria, helminths, protozoa, spores, inorganic molecules, organic molecules or mixtures thereof. In one example, the contaminants are bacteria species or pathogenic bacteria species.

Using the device and the cartridge of the present invention any kind of bacteria can be detected. Such bacteria can be gram-positive or gram-negative bacteria or archaea. Examples of such bacteria include, but are not limited to *Bacillus anthracis, Brucella melitensis, Campylobacter jejuni, Campylobacter coli, Clostridium botulinum, Coxiella burnetti, Cornyebacterium diphtheriae, Escherichia coli, Escherichia coli* O157:H7, *Enterococcus faecalis, Francisella (Pasteurella) tularensis, Legionella pneumophila, Mycobacterium tuberculosis, Proteus vulgaris, Neisseria meningitis, Brucella militensis, Rickettsia rickettsi, Salmonella paratyphi, Salmonella typhimurium, Salmonella typhi, Shigella dysenteriae, Staphylococcus aureus, Streptococcus pneumoniae, Treponema pallidum, Vibro cholerae, Yersinia pestis, Yersinia enterocolitica*, mixtures or subspecies thereof. A group of particular interest is the group comprising *Salmonella* sp., *Escherichia coli, Staphylococcus aureus, Campylobacter jejuni, Campylobacter coli* and *Bacillus cereus* which are responsible for a large percentage of diseases caused by bacteria (Ivnitski, D., Abdel-Hamid, I., et al., 1999, Biosensors & Bioelectronics, vol. 14, p. 599).

Another specific group of particular interest is the group of coliform bacteria which is used extensively as an indicator of water quality. Thus, in one example the contaminant to be detected is a coliform bacterium. Most coliforms are present in large numbers among the intestinal flora of humans and other warm-blooded animals, and are thus found in fecal wastes. As a consequence, coliforms, detected in higher concentrations than pathogenic bacteria, are used as an index of the potential presence of entero-pathogens in water environments. Coliforms are also routinely found in diversified natural environments, as some of them are of telluric origin, but drinking water is not a natural environment for them. Their presence in drinking water must at least be considered as a possible threat or indicative of microbiological water quality deterioration.

The definition of coliforms (Rompré, A., Servais, P., et al., 2002, supra) used herein is the one set forth in Standard Methods for the Examination of Water and Wastewater (Part 9221 and 9222; APHA et al., 1998), coliform group members are described as:
1. all aerobic and facultative anaerobic, gram-negative, non-spore-forming, rod-shaped bacteria that ferment lactose with gas and acid formation within 48 h at 35° C. (multiple-tube fermentation technique; Section 3.1) or 2. all aerobic and many facultative anaerobic, gram-negative, non-spore-forming, rod-shaped bacteria that develop a red colony with a metallic sheen within 24 h at 35° C. on an endo-type medium containing lactose (membrane filter technique; Section 3.2). The definition of members of the coliform group can be extended to include other characteristics, such as β-D-galactosidase-positive reactions (Part 9223; APHA et al., 1998) (enzyme substrate test, Section 4.2). The search for β-galactosidase-positive and β-galactoside-permease-positive organisms also permits a confirmation step for lactose fermentation, when the multiple-tube fermentation technique is used. The cytochrome-oxidase test is also used as a confirmation test to eliminate some bacteria of the *Aeromonas* or *Pseudomonas* genera that would ferment lactose.

Typical genera which belong to the group of coliform bacteria include, but are not limited to *Citrobacter, Enterobacter, Escherichia, Hafnia, Klebsiella, Serratia* and *Yersinia*. Well known coliform bacteria are *Escherichia coli* and *Enterobacter aerogenes*.

Protozoa are unicellular eukaryotes. They are relatively large and some are visible with the naked eye. They occupy a vast array of habitats and niches and have organelles similar to those found in other eukaryotic cells as well as specialized organelles. Subgroups belonging to the group of protozoa are flagellates, amoebae, sporozoans and ciliates. Pathogenic genera and organism of protozoa which can be found in liquid streams include, but are not limited to *Naegleria* spp., *Entamoeaba histolytica, Giardia lamblia, Cryptosporidium parvum* and *Cyclospora* spp.

Examples of pathogenic cyanobacteria include, but are not limited to species of the genus *Microcystis* which can cause diarrhea from ingestion of the toxins these organisms produce, *Anabaena* which produces a microcystin toxin implicated in liver damage and *Aphantiomenon*. Examples of helminths include, but are not limited to *Ascaris lumbricoides, Trichuris trichiora, Taenia saginata* and *Schistosoma mansoni*.

Examples of viruses include, but are not limited to enteroviruses (polio, echo, coxsackie), Hepatitis A and E, Norwalk viruses, Sapporo, Rotavirus, Astroviruses, Adenovirus and Reovirus. An example of spores would include microsporidian spores. Spores can be produced by bacteria as well as by protozoa. For example, the pathogenic protozoa *Cryptosporidium* has also a spore phase (oocyst) and in this state can survive for lengthy periods.

The inorganic and organic molecules consist mainly of toxins which are produced by microorganism such as bacteria, protozoa, cyanobacteria and helminths. Toxins may exert their effects directly on a target cell or may interact with cells of the immune system resulting in the release of immunological mediators (cytokines) (Deisingh, A. K., Thompson, M., 2002, Analyst, vol. 127, p. 567). Two major types of toxin have been described: endotoxin, which is a component of the outer membrane of gram-negative bacteria and exotoxins, which are produced extracellularly by both gram-positive and gram-negative bacteria.

Endotoxin, also called lipopolysaccharide (LPS), is a component of the outer membrane of gram-negative bacteria and is released from the bacterial surface following lysis of the bacterium. Endotoxins are responsible for endotoxic shock, a syndrome exhibiting a high mortality, particularly in immunocompromised individuals. By contrast, exotoxins are diffusible proteins secreted into the external medium by the pathogen. One group of exotoxins is the enterotoxins, which cause symptoms of gastro-intestinal disease, including diarrhoea, dysentery or vomiting. Botulinal toxins are among the most poisonous natural substances known. Seven main types of *C. botulinum* designated A-G produce antigenically distinct toxins with pharmacologically identical actions. Types A, B and E are those most frequently associated with human disease, but all types can cause disease.

*E. coli* O157+H7 is an example of a verocytotoxigenic bacterium in that it produces a toxin which is harmful to cultured vero cells (African green monkey kidney cells). This verocytotoxin (VT) is composed of two parts, VT-1 and VT-2 with each having A and B subunits. The A subunit possesses the biological activities of the toxin while the B subunit mediates specific binding and receptor-mediated uptake of the toxin.

Toxins from non natural sources like man-made toxins can also be detected using the devices of the present invention. For example, in some countries the biocide 4,4'-dichlorodiphenyl-1,1,1-trichloroethane (DDT) which is also a toxin which accumulates in the animal or human body is still used and can therefore be found in the water.

Using the device and the cartridge of the present invention contaminants can be detected and/or removed from a liquid stream which is a processed water stream. A processed water stream means for example wastewater, water from the ballast tank of ships, sea water, river water, brackwater and drinking water. For example, using the online system of the present invention to provide for a fast detection of contaminants in the water of the ballast tanks of ships can save time and thus money because the ships do not have to wait before entering the harbor for any test results because the system of the present invention allows screening of large volumes in a short time and provides immediate results upon detection of a contaminant.

Referring now to FIG. 2 an example of a continuous flow device suitable for detecting and/or removing of at least one contaminant is exemplarily described in more detail. The contaminant to be detected in this exemplary device is a bacteria cell. As can be seen from FIG. 2, a continuous flow device can be composed of three distinct subsections; optical, fluidic and monitorisation. The optical region of the device provides the bacterial detection capability whilst the fluidic section simulates domestic water flow dynamics. Monitorisation offers complete control of the component parts of the device, image collection, analysis of images captured by the optical region and the flagging and alert system of the pathogen detector. This exemplary device is intended for the detection of pathogenic spores or pathogenic indicators including *Escherichia coli* and *Enterococcus faecalis*.

In addition to the capture molecules immobilized on the optically transparent support material further molecules such as, but not limited to, enzymes, aptamers and the organisms themselves can be immobilized on the support material. Such further molecules can assist in removing and/or cleaning the liquid stream from, for example, toxic substances. They can be used for example to detoxify water flows by the capture or breakdown of various molecules, especially biomolecules. Therefore, a feasible alternative application of the device includes the bioremediation of liquid flows (Chen, B. Y., Chen, S. Y., et al., 2006, Process Biochemistry, vol. 41, p. 1574). In addition, biodegradation of chemical substances, bio-separations, sample purification, enrichment and filtration are all possible with the devices described herein (Tombelli, S., Minunni, M., 2005, Biosensors and Bioelectronics, vol. 20, p. 2424; Van Emona J. M., Gerlach, C. L., et al., 1998, Journal of Chromatography B, vol. 715, p. 211.

The optical region also comprises the flow through cartridge (A), specially fabricated in quartz, which contains beads which effectively filters water in flow pipes for specific bacteria and is central to the whole detection device. The cartridge is the only component of the detection device that plays a role in both the optical and fluidic sections of the device. The bead comprising cartridge provides the device the ability to sample and to prepare the sample whilst simultaneously lending itself to a complete optical analysis, providing optimal pathogen detection.

The beads of the exemplary cartridge (A) in FIG. 2 have fluorescently tagged antibodies or antibody fragments specific to the bacteria of interest immobilized on their surface.

In this example, the beads are made of glass. The immobilized antibodies provide the specificity of the online detection device by binding to organisms to which they are complimentary. Organisms of no interest pass the immobilized antibodies with no effects.

Turning now to the optics section, a controlled UV/VIS light (or electromagnetic radiation, EMR) originating from either a laser or photodiode (K) is directed through and reflected off optical components towards the bead containing cartridge. After exiting the EMR source UV/VIS light immediately passes a neutral density filter (J). The neutral density filter (J) provides the option of varying the power of the directed EMR. The EMR is then guided by a 45° mirror (I) into a focusing lens (H) which widens the diameter of the EMR beam. A collector lens (G) straightens and directs the beam to a dichroic mirror (C) which reflects the beam through an objective lens (B) (attached to a linear translation stage) (L) onto the cartridge comprising beads (A). The translation stage (L) moves the objective lens (B) backwards and forwards to enable resolution of a series of planes throughout the depth of the cartridge (A).

In one example, the objective lens (B) used in a continuous flow device is a CFI L plan EPI 20×CR by Nikon (NA 0.45; W.D. (mm) 10.9-10-0; Focal length (mm) 10.00; Physical depth of focus 1.36 µm). Other objectives from this CR series can also be used.

Specific features of an objective to be used in a device of the present invention include the ability to transmit the excitation light, such as UV light with little effect to the quality of lens housed within the objective. The objective has a long working distance with relatively high numerical aperture. The long working distance permits analysis of the full depth of the cartridge, and the relatively high numerical aperture enables the objective to accept light from broad fields, increasing the chances of the light emitted by the reporter groups being captured.

In one aspect the device further comprises an additional lens positioned directly in front of the cartridge which widens the diameter of the radiation beam before entering the cartridge so that the radiation beam enters into cartridge over a broader space, i.e. more reporter groups can be reached and excitated. This feature is illustratively shown in FIG. 5 where a laser beam is widened by lenses 2 (concave lens) and 3 (convex lens) before entering the cartridge through the incident wall portion. These lenses 2 and 3 are used to refine and broaden the laser width. 5 is a fibre optic or wave guide within which emitted light from the fluorophores is transmitted.

The translation stage (L) or micromanipulator are instruments that allow the movement of the objective (B) and bead comprising cartridge (A) over very small distances very accurately with high repeatability. The use of the micromanipulators provides the possibility of imaging the entire bead comprising cartridge during the water flow process. The step movements of the micromanipulators are harmonized with the image acquisition by the charged couple device (CCD) (F).

A percentage of quantum dots (red) (labeled to the antibodies as reporter group) and bacteria (blue/green) fluorescence travels back to and through the objective lens (B) with any reflected signal from the UV/VIS beam itself. The laser signal is reflected again by the dichroic mirror (C) whilst the green/blue and red are transmitted through the mirror (C). A subsequent short pass filter (D) removes any red fluorescence whilst the bacterial fluorescence is focused and transmitted to the sensitive region of the charged couple device (F) via a focusing lens (E).

Turning now to the fluidic section shown in FIG. 2, the flow of water through a bead comprising cartridge begins at the reactor vessel (3) and is controlled by a peristaltic pump (2). The pump (2) can be tuned for a range of flow velocities. The water flow arrives at the bead comprising cartridge (A) which is clipped onto the translation stage (L). The stage (L) moves vertically and laterally to a sub-micron level. The flow passes through the cartridge and is subsequently monitored by a flow measuring device (1). The flow then passes into either a collection facility or back into the reaction vessel (3) for further cycling. The flow measuring device (1), the reaction vessel (3) and the pump (2) are optional parts which are mainly included for characterization of the device. Using it on an industrial level, the water flow can be redirected from a main pipe directly through another pipe set off the main pipe to the cartridge. After passing the cartridge the water can be discarded to avoid any contamination of the water flowing through the main pipe with particles possibly coming out of the cartridge.

The monitoring section of the device which is shown in FIG. 2 can be a computer (c) running a software for analyzing the data. The software, for example LabVIEW™ software, can control several of the devices component parts including; the pump (2), flow meter (1), translation tables (L), the laser or photodiode (K) and the charged coupled device (F). This will provide complete control of the device at one source. The computer (C) also provides online analysis of images captured by the CCD (F). On bacterial detection the software halts the flow of water whilst simultaneously transmitting a signal alert to key people. FIG. 2 also shows a display monitor (b) for signal output to the user and an acquisition card and digital analogue converter stack (a). The acquisition card and digital analogue converter stack (a) is a convenient arrangement for signal converter cards. Each instrument that is controlled will send a signal to a pre-selected card for signal transduction or alteration. This will predispose the signals into a format understood by the analyzing software, for example LabVIEW™ software, thus giving greater control of the entire detection device.

In another aspect, the present invention refers to a continuous flow device suitable for detecting and/or removing of at least one contaminant in a liquid stream, comprising:
  a) at least one rotatable support positioned within the liquid stream comprising molecules for capturing the at least one contaminant wherein the capture molecules are immobilized on the surface of the rotatable support;
     wherein each of the capture molecules further comprises at least one reporter group which emits a signal upon binding of the at least one contaminant;
  b) at least one radiation source emitting a radiation beam for excitation of the at least one reporter group;
  c) at least one detector for detecting the signal emitted by the at least one reporter group.

Figure 6:
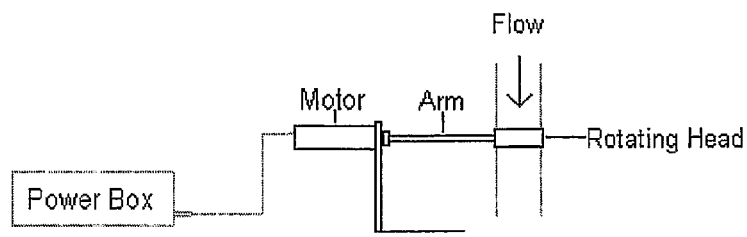
FIG. 6 illustrates the assembly of a part of a device using a rotatable support instead of a cartridge to capture the contaminants.
Figure 7A:
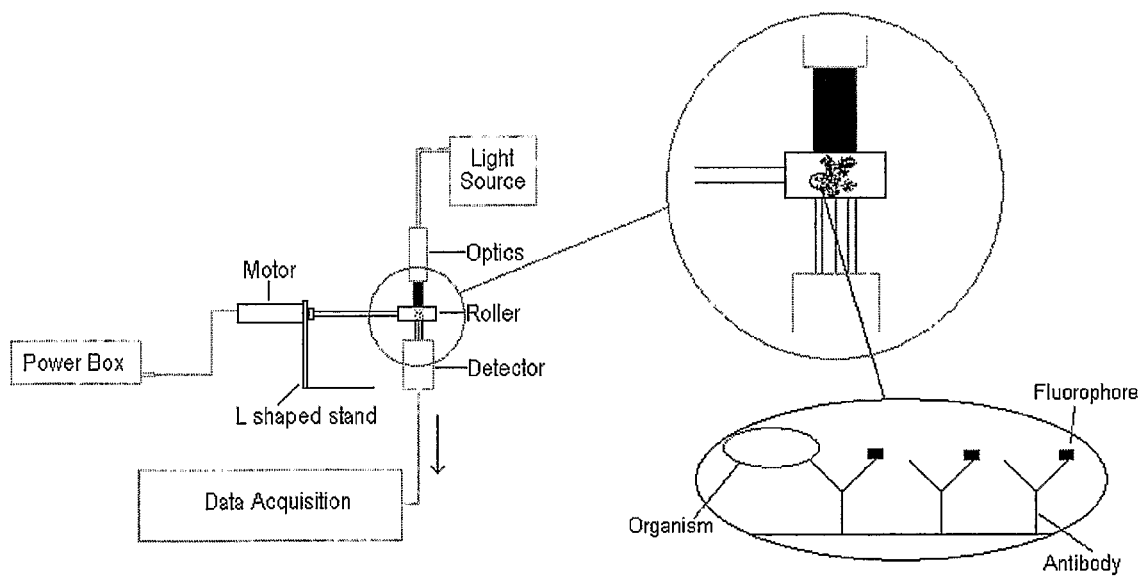
FIG. 7A illustrates not only the assembly of the device referred to in FIG. 6 but shows also the optical section of the device using a rotatable support. The way of the radiation/light is indicated by an arrow. In the example of the device illustrated in FIG. 7A antibodies are used as capture molecules which are linked to a fluorophore that emits a signal upon binding of a microorganism to the capture group. This signal emitted by the reporter group is measured by the detector and transferred to the monitoring section carrying out the data acquisition and processing. In case contaminants are detected the water flow in the main pipe can be stopped.
Figure 7B:
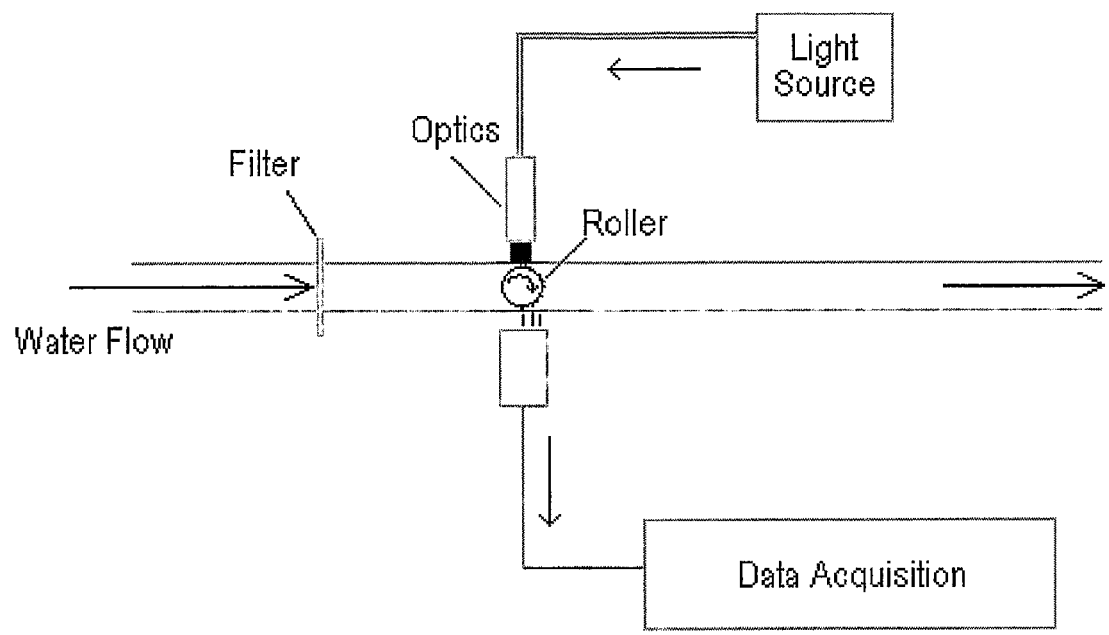
FIG. 7B shows the device of FIG. 7A in an offset view. The way of the radiation as well as the flow direction of the liquid stream are indicated by arrows. This Figure illustrates in more detail the layout of the single components relative to each other. The excitation radiation enters the pipe through an incident wall portion of the pipe wherein the pipe is positioned perpendicular to the optical system of the device. It should be noted that the direction of rotation of the rotatable support follows the direction of the liquid stream in the pipe. However, it is also possible that the rotatable support rotates against the direction of the liquid stream.

A difference between this device of which an exemplary set up is illustrated in FIGS. 6 and 7A and 7B and the device shown in FIGS. 1 and 2 lies in the fact that no cartridge is used comprising support material with capture molecules immobilized thereon but a rotatable support on which the capture molecules are immobilized. Rotation of the support provides a bigger surface for the attachment of contaminants. Furthermore, use of a rotatable support has the effect that the radiation does not has to pass through a cartridge but only a short distance of about a few millimeter (about 1 to 5 mm) through the liquid stream (see therefore the side view of an exemplary device in FIG. 7B). The radiation also enters and exits the pipes comprising the rotatable support through at least one radiation incident wall portion and at least one emerging wall portion.

Similar as for the cartridge also the rotatable support serves three different purposes. Firstly, the rotatable support traps contaminants contained in the liquid stream flowing over the surface of the rotatable support (enrichment of contaminants). Secondly, the mechanism used to trap or catch the contaminants on the rotatable support via the capture molecules simultaneously provides the mechanism of signaling on contaminant attachment to the capture molecules (sample preparation). The sensitive signal detector is positioned strategically so that any signal sent from the matrix comprising the capture molecule binding the contaminant is captured immediately (microorganism detection). The specificity of the capture molecule further enables to identify the organisms trapped in the matrix directly.

The radiations beam from the radiation source and the emitted radiation exit and enter the liquid stream at the same or at different positions. In one example illustrated in FIG. 7B, the rotatable support is situated in the path of a flowing liquid stream whilst constantly rotating. Perpendicular to the flow of the liquid stream a radiation source is directed towards the rotatable support on which the capture molecules are immobilized. On the side of the rotatable support directly opposite the radiation source a detector is situated which detects radiation emitted by the reporter groups linked to the capture molecules which are immobilized on the rotatable support. It becomes also apparent from those Figures that the pipe in which the liquid stream flows comprises a radiation incident wall portion and a radiation emerging wall portion to allow radiation to enter and exit the pipe comprising the rotatable support.

In another example, the position of the radiation source and the detector is congruent which means that the radiation beam from the radiation source and the emitted radiation exit and enter the liquid stream at the same position. In this case, similar to the device using the cartridge, the side of the pipe opposite the radiation incident wall portion and the radiation emerging wall portion can be coated with a reflective material to allow redirection of radiation emitted from the reporter group towards the detector.

In another example, the rotatable support itself serves as radiation conductor. That means that the radiation does not enter the pipe through a radiation incident wall portion but through the rotatable support. At the same time the rotatable support also redirects light emitted from the reporter groups to the detector. When using the rotatable support for conducting the radiation from the radiation source as well as the radiation emitted from the reporter groups it is another advantage that measurement can also be taken from detritus water because the excitation radiation as well as the emitted radiation do not have to pass through the water body when coming directly from the rotatable support. In case the rotatable support acts as the radiation conductor it can be made of the same material as the optically transparent support material loaded in the cartridge described above.

The rotatable support can be of any shape as long as it can rotate within the pipe for the liquid stream. For example, the rotatable support can have the shape of a thin plate or a cylindrical shape (like a barrel). The size of the rotatable support can be between about 1 cm to about 1 m, 1 cm to about 10 cm or even below and above those values.

In case the radiation enters the pipe through a radiation incident wall portion and exits it through a radiation emerging wall portion the rotatable support on which the capture molecules are immobilized can but does not need to be manufacture of another material than the optically transparent support material. That means that the rotatable support does not necessarily need to be manufacture of optically transparent materials. Thus, any kind of material which allows immobilization of capture molecules on its surface can be used for the rotatable support. In addition to the material cited above for the optically transparent support material such material can further include, but is not limited to metals, such as gold, silicone or platinum, polymers such as polyacrylamide, methacrylate or polystyrene.

Immobilization of capture molecules on such surfaces can be carried out as described above. In addition, protein A, protein G or a streptavidin-biotin complex (for more details see above) are commonly used to immobilize capture molecules, such as antibodies, on metal surfaces, such as gold and platinum. Primarily metals are functionalized so that its surface presents a layer of either amine, thiol, carboxyl or aldehyde groups. These groups provide the best opportunity for covalent bonding with antibodies. Any linkers providing such functionalities would be useful and such linkers are known in the art. Some of them have been already described above (see e.g. streptavidin-biotin system).

Depending on the application it is also possible to position several rotatable supports in a pipe to further increase the likelihood of capturing contaminants in particular if the liquid stream monitored is known for transporting small amounts of contaminants. It is also possible to combine the device with the rotatable support together with the device using the cartridge as described above. The optical section of the device using the rotatable support is the same as the one using the cartridge so that both systems can be easily combined.

In general, all comments made above in connection with the cartridge (e.g. capture molecules, immobilization on the surface, binding tags, etc.) also apply to the device using the rotatable support.

In another aspect the present invention is directed to a continuous flow method suitable for detecting and/or removing of at least one contaminant from a liquid stream using a device according to the present invention, wherein the method comprises directing a liquid stream along or through such a device. Since the activity of some of the capture molecules might depend on the pH value and the temperature of the liquid stream the method of the present invention can also comprise adjusting the temperature and/or pH value of the liquid stream in order to allow the capture molecules to work in their optimal range. For example, when antibodies are used the pH value would be in the range of about 4 to about 8 or 6.5 to about 7.5 while the temperature range would be between about 10° C. to about 38° C. or 22° C. to about 38° C.

The flow rate which can be used in the method of the present invention is much higher than in usual flow devices like a flow cytometer. The flow rate which can be used in the method of the present invention is between about 100 ml/min to about 2 l/min while in another example the flow rate is between about 500 ml/min to about 2 l/min.

As previously mentioned it may be suitable to locate the devices of the present invention off the main pipe in which the liquid stream flows. Thus, the method of the present invention comprises locating the device in a pipe which runs parallel to the main pipe and branches off a certain amount of the liquid stream which is supposed to be screened for contaminants.

The present invention is also direct to the use of the devices and the method of the present invention to detect and/or remove contaminants from a liquid stream.

In another aspect, the present invention also refers to a cartridge adapted to be used in a continuous flow device suitable for detecting and/or removing of at least one contaminant in a liquid stream, wherein the cartridge comprises:
a circumferential wall having a first inlet and a first outlet for the liquid stream and a radiation incident wall portion and a radiation emerging wall portion;
wherein the cartridge further comprises or is packed with optically transparent support material;
wherein the optically transparent support material is packed in the cartridge such that a liquid stream can pass between voids formed within and/or by the optically transparent support material;
wherein the optically transparent support material comprises molecules for capturing at least one contaminant,
wherein the capture molecules are immobilized on the surface of the support material;
wherein each of the capture molecules further comprises at least one reporter group which emits a signal upon binding of the at least one contaminant.

In another aspect, the present invention also features a rotatable support adapted to be used in a continuous flow device suitable for detecting and/or removing of at least one contaminant in a liquid stream wherein the rotatable support comprises molecules for capturing at least one contaminant wherein the capture molecules are immobilized on the surface of the rotatable support; and wherein each of the capture molecules further comprises at least one reporter group which emits a signal upon binding of the at least one contaminant.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Chemicals and Reagents Used for Functionalisation, Antibody Immobilisation and Conjugation 5% $HNO_3$, distilled water, 3-aminopropyltrimethoxysilane (APTS) (10% v/v), 6 N HCl, Glutaraldehyde (GA) 2.5% (Chemicals Testing and Calibration Laboratory, Singapore), 0.05 M, 0.1 M phosphate buffer pH 7, 0.01 phosphate buffer saline pH 7.2 (1st Base International LTD, Singapore), antibodies (Abeam, US), Qdots$^{-streptavidin}$ 655, (Invitrogen, Singapore) and Rabbit Anti $E.\ coli^{-Biotin}$, O and K antigenic serotypes (Abeam, US).

Glass Functionalisation Method (APTS-GA): for Antibody Immobilisation

Glass slides (borosilicate, Cell Path, UK) and glass beads (6 mm diameter, borosilicate, Corning, US) are washed in 5% $HNO_3$ at 80-90° C. for 60 min and then rinsed with distilled water and dried in an oven for 24 hr at 110° C. Glass beads or glass slides are immersed in 10% (v/v) APTS, pH is adjusted to between 2 to 3 with 6 N HCl. Glass in APTS is placed into an incubation bath at 75° C. for 2 hours. The silanized glass is removed from the bath, washed with distilled water and dried over night in an oven at 110° C. The glass substrate is then submerged in 50 ml glutaraldehyde (2.5%) in 0.05 M phosphate buffer pH 7 for 60 minutes, see FIG. 8.

Figure 10:
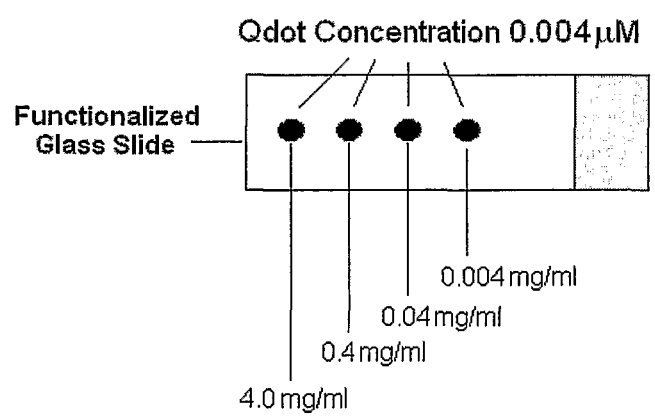
FIG. 10 illustrates a step in the experiment carried out for the functionalization of glass slides. For more details see section "Glass Functionalisation Method (APTS-GA): For antibody Immobilisation" in the experimental section of the application.

The glass substrates are then washed with the same phosphate buffer. The antibody/biotin solution is aliquoted in serial dilution onto the functionalised glass substrate and stored at 4° C. over night. The glass substrate is washed with 0.01M phosphate buffer saline (PBS) pH 7.2 three times. 10 µl of a predetermined concentration of the Qdot streptavidin conjugate is applied to each region of the glass substrates that held the antibody. The glass substrates are then allowed to stand for 30 minutes (Biotin-XX microscale protein labeling kit (MP30010) online manual, Molecular Probes, Invitrogen; Qdot streptavidin conjugates online manual, molecular probes (MP 19000), Molecular Probes, Invitrogen; Gomez J. L. et al., 2006, Enzyme and Microbial Technology, vol. 39, p. 1016). See FIG. 10. The glass substrates are then washed vigorously in 0.01 M PBS pH 7.2 three times and subsequently ready for bacterial analysis.

X-Ray Photoelectron Spectroscopy: for Analysing Glass Surface Chemistry

Samples are prepared by cutting the glass slides into 0.5 cm by 0.5 cm pieces and functionalized with the method described in section 1.2. X-ray photoelectron spectra of a blank and functionalised glass surface are collected with a Axis-Ultra photoelectron spectrometer (Kratos Analytical, Japan) with a monochromatized Z-ray Al-Kα radiation source (1486.7 eV) at 15 kV and 10 mA. The analysis is carried out under high vacuum and pressure in the analysis chamber, approximately $3\times10^{-9}$ Torr ($3.9997\times10^{-7}$ Pascal). The pass energy is set to 40 eV for detailed studies. Binding energies are calibrated with respect to alkyl C1s signal at 284.6 eV.

Atomic Force Microscopy: for Imaging Qdots and Bacteria

The atomic force microscope (AFM) used to image qdots and bacteria, $E.\ coli$ K12 (ATCC 23716), on the glass substrates is a Dimension 3100 series Scanning Probe Microscope (Veeco, Digital Instruments, US) with duel monitored computer, Nanoscope III SPM Controller, Nanoscope 5.12r5 software. A cantilever with a force constant of 0.06 N/m is used to scan the samples in contact mode.

Bacterial Culture $Escherichia\ coli$ K12 (ATCC 23716) is prepared by inoculating 20 ml of tryptic soy broth (TSB) with $E.\ coli$ K12 colonies grown on tryptic soy agar plates for 24 hours. The 20 ml culture has been incubated in a water bath (type GR150, Grant Instruments, Cambridge, UK) over night at 37° C. at 100 rpm. The following morning 100 µl of the freshly grown culture is used to inoculate a second 20 ml volume of TSB and allowed to incubate in the same water bath and same conditions for 2 hours. Cells are harvested after 2 hours whilst they are at the exponential phase of growth. The cells are taken from the bath and centrifuged at 3166*g for 10 minutes (Centrifuge Model No. 5810R, Eppendorf, Germany). The bacteria are washed twice in PBS after which they are re-immersed in PBS ready for analysis.

Flow Cytometry: for Bacteria Capture Studies

Small cut glass slides approximately 0.5 cm by 0.5 cm are functionalised as in the method described in section 1.2. 20 μl of predetermined antibody concentrations (Rabbit Anti $E.$ $coli^{-Biotin}$, O and K antigenic serotypes, Abeam, US) are immobilized onto the substrates in serial dilution which are then incubated at 4° C. over night. The samples are then washed in 0.01 PBS and exposed to a known concentration of $E.$ $coli$ K12 (ATCC 23716) for 30 minutes. The small cut glass with cell samples are place into a 15 ml centrifuge tube containing 3 mls of 0.01 PBS for one minute. The un-immobilized bacteria fell into the PBS and the immobilized bacteria stayed attached to the glass slides. After one minute the glass slides are then taken from the tubes with care, removing as little bacteria +PBS as possible. The 15 ml tubes are then centrifuged at 3166*g for 10 min (Centrifuge Model No. 5810R, Eppendorf, Germany), supernatant decanted and bacterial pellet re-immersed in 1 ml 0.01 PBS.

After agitation 10 μl of SYBR green nucleic acid dye (Invitrogen, Singapore) is introduced to each cell sample and left in a dark cupboard to incubate for 10 mins. Cell concentration of each sample has been determined using flow cytometry (FACScalibur, Becton Dickinson, Singapore).

Glass Bead Preparation

Figure 11:
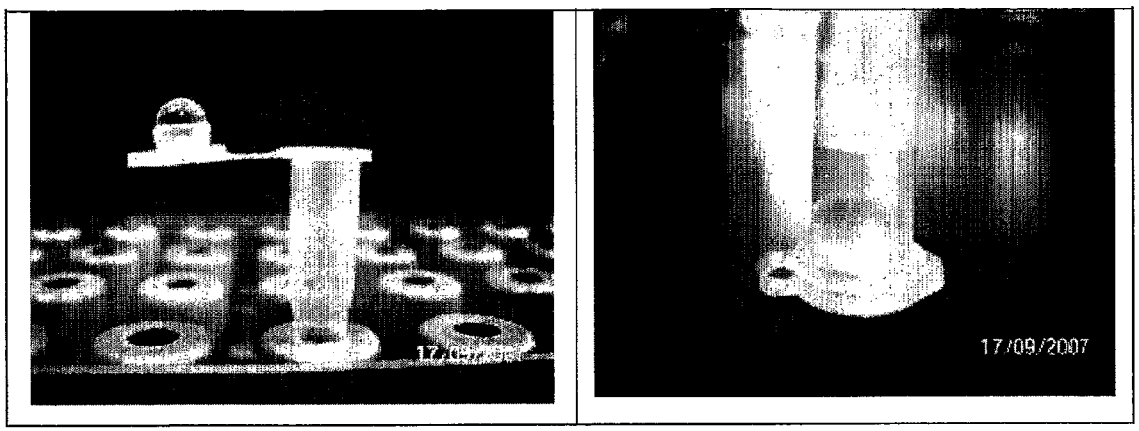
FIG. 11 shows glass beads immersed in antibody sample (capture molecule)
Figure 12:
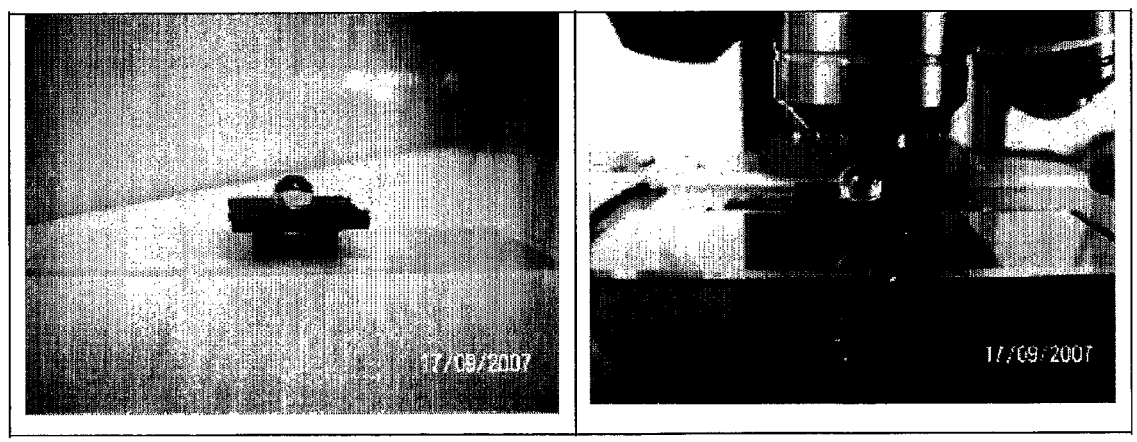
FIG. 12 shows microscopy of bacteria (contaminants) immobilised by antibodies (capture molecule) attached to a glass bead (solid support).

Functionalisation of glass beads is carried out using the same chemistries used for the glass slides, see section 2.1. A series of antibody dilutions (Rabbit Anti $E.$ $coli^{-Biotin}$, O and K antigenic serotypes, Abeam, US) are prepared in small centrifuge tubes, 100 μl per tube. The dilutions are thoroughly mixed before immersing one functionalised glass bead into the antibodies, see FIG. 11. The beads in antibody tubes are incubated at 4° C. overnight. After incubation, the beads are removed and washed in 0.01 M PBS and placed into a second centrifuge tube containing 100 μl of a predetermined concentration of Qdot$^{-streptavidin}$ solution. The Qdots conjugated to the immobilised antibodies for 30 minutes, after which the beads are retrieved and washed in 0.01 M of PBS. The prepared beads are then exposed to a bacterial culture of $E.$ $coli$ K12, washed in 0.01 PBS and examined using epifluorescence microscopy. The bead is stabilised onto the microscope stage with the use of a small plastic table device, see FIG. 12.

Epifluorescence Microscopy

Immobilised cells are observed using an Olympus BX60 microscope at 1000× using UV and Blue band pass filters. Images are taken using an Olympus charged coupled device, type PM-VB-3. Images are analysed using Image Pro Plus, Media Cybernetics, US.

Results and Discussion

X-Ray Photon Spectroscopy

High resolution XPS revealed contrasting quantities of carbon, nitrogen and silicone species (found at consistent levels of binding energies (eV)) between the APTS-GA treated and untreated glass surfaces, see Table 1. FIG. 13 reveals the same information as shown in Table 1 in the form of spectra and shows the presence of 3 carbon components: an aliphatic C—C component with a binding energy of 285.0 eV, a C-0 component at 286.5 eV and a C=O component at 288.8. The main peak at 285.0 eV represents aliphatic carbons likely to originate from contaminating carbon sources and from the covalently bonded carbon atoms found within the branch structures of the APTS-GA combination. Functionalisation of the surface by the APTS-GA chemistries sees a total increase in atomic carbon of 8.92%. A tripling of nitrogen species (0.25% to 0.79%) suggests the presence of amino groups after functionalisation. This combined with a slight reduction on the atomic concentration of surface silicone (20.77% to 19.64%) increases the confidence that the glass surface chemistry has been modified appropriately by the functionalisation chemistries. The signal increase of N1s (400 eV) and the C1s peak at (287 eV) suggest that the glass surface has been covalently linked with the APTS-GA.

TABLE 1

Atomic concentration percentages of nitrogen, carbon and silicone species on the untreated and APTS-GA treated slides, by XPS.

| Element | Blank. Atomic concentration % | APTS-GA Atomic concentration % | Binding energy position (eV) |
|---|---|---|---|
| N 1s1 | 0.25 | 0.79 | 400.00 |
| C 1s1 | 18.49 | 22.91 | 285.00 |
| C 1s2 | 4.72 | 7.72 | 287.00 |
| C 1s3 | 1.36 | 2.86 | 289.00 |
| Si | 20.77 | 19.64 | 103.00 |

Confirmation of Antibody Immobilisation by Flow Cytometry

Figure 14:
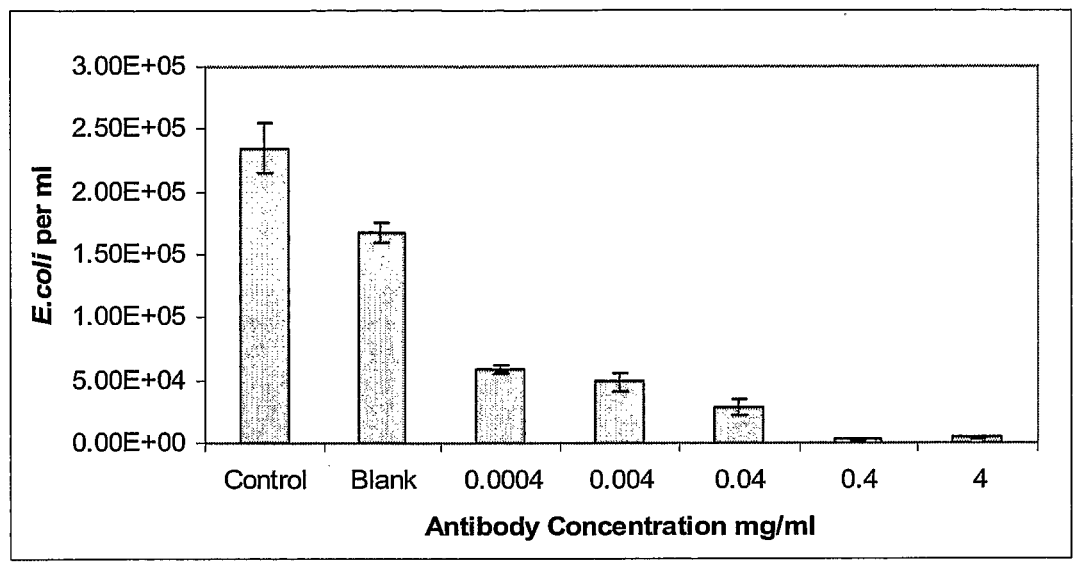
FIG. 14 demonstrates the success of antibody immobilisation which has been confirmed by enumerating the amount of bacteria that didn't stick to the glass slides (solid bars in FIG. 14) as opposed to how many that did. Approximately 235.000 cells have been introduced to a series of cut slides onto which serially diluted antibodies have been immobilised. Five different concentrations of antibodies have been used, 4 mg/ml through to 0.0004 mg/ml. A functionalised slide without antibodies has been used as a "blank" and the stock culture applied to the slides has been used as a "control". The results presented do suggest that the functionalisation chemistries work and that the antibodies also work.

Success of antibody immobilisation is confirmed by enumerating the amount of bacteria that did not stick to the glass slides as opposed to how many that did. Approximately 235,000 cells have been introduced to a series of cut slides onto which serially diluted antibodies have been immobilised using the chemistries discussed above. Five concentrations of antibodies are used: 4 mg/ml through to 0.0004 mg/ml. Functionalised slides without antibodies are used as a blank and the stock culture applied to the slides is used as a control, see FIG. 14.

The blank seems to attract approximately 35,000 cells, but it is believed that a number of these cells are lost when retrieving the glass slides from the wash tubes. As much as 20% of the cells are lost in slide removal or by means of attachment to the slides regardless of antibody presence. The experiment, carried out in triplicate, reveals, as might be expected, a decrease in bacterial detachment as the antibody concentration decreases. 4 mg/ml of antibody see approximately 230,000±921 cells retained on the glass slide (98%). This is in stark contrast to the blank slide that saw approximately 67355±7689 cells attached (29%). The difference between the two slides is indicative of the usefulness of the antibodies used and the presence of non-specific binding. The latter of which could be addressed by the treatment of slides with surfactant. The small differences of bacterial attachment between 4 mg/ml and 0.4 mg/ml may suggest that the capacity of the 4 mg/ml has not been met by the population of cells used. Or it may reveal that the optimum concentration of antibodies for the immobilisation is not necessarily the most concentrate. Slightly higher concentrations of bacteria could be used to improve the immobilisation experiment, although not to high. The results presented do suggest that the functionalisation chemistries work and that the antibodies also work.

Atomic Force Microscopy

Figure 15:
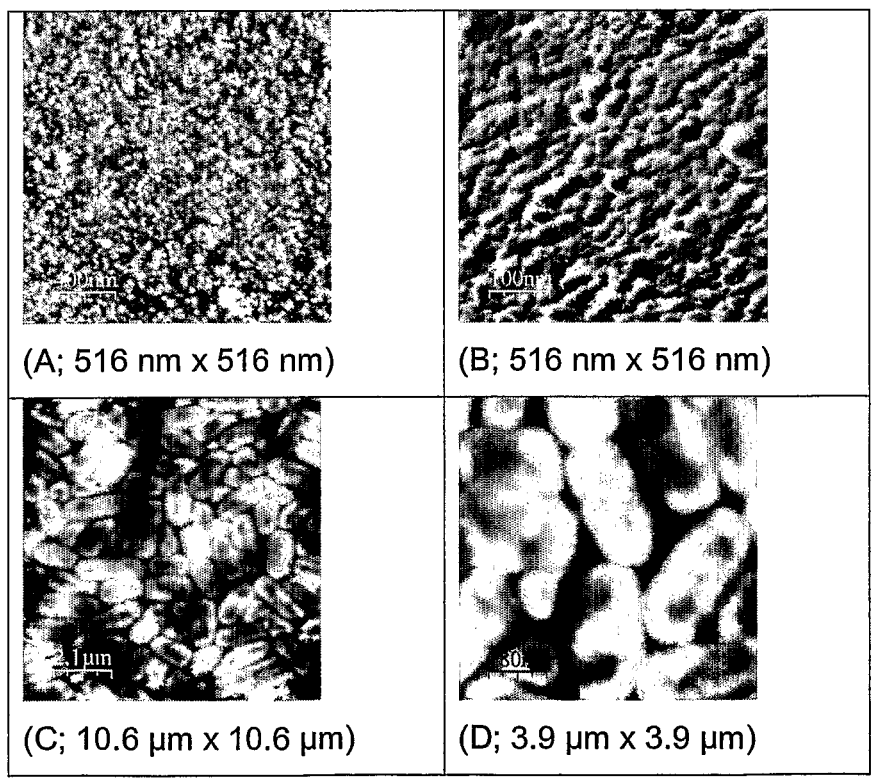
FIG. 15 shows atomic force pictures of quantum dots (Qdots) (Qdots alone FIG. 15A, B and *E. coli* K12 with Qdots FIG. 15 C,D) which can be used as reporter groups in the devices of the present invention. The Qdots used to highlight the bacteria fluoresce at 655 nm, red under blue excitation. When they interact with the bacteria the cells fluoresce green. The bacteria without Qdots do not fluoresce under blue excitation or fluoresce very little. As can be seen from FIG. 15 atomic force microscope (AFM) is sensitive enough to image the qdots and an interaction with the bacteria, see FIG. 15 (D), expand the image. These images reveal that the antibodies conjugated to the qdots still have the ability to bind the bacteria to the surface. Below the single pictures A, B, C and D the total measurement of each of the pictures has been given.

AFM enables the visualisation of very small particles, for example Qdots. The Qdots used to highlight the bacteria fluoresce at 655 nm, red under blue excitation. When they interact with the bacteria the cells fluoresce green. The bacteria without Qdots do not fluoresce under blue excitation or fluoresce very little, as seen later. AFM is sensitive enough to image the qdots, see FIG. 15, and their interaction with bacteria, see FIG. 15 (D), expand the image. These images reveal that the antibodies conjugated to the qdots still have the ability to bind the bacteria to the surface.

Epiflourescence Microscopy of Glass Slides

Figure 16:
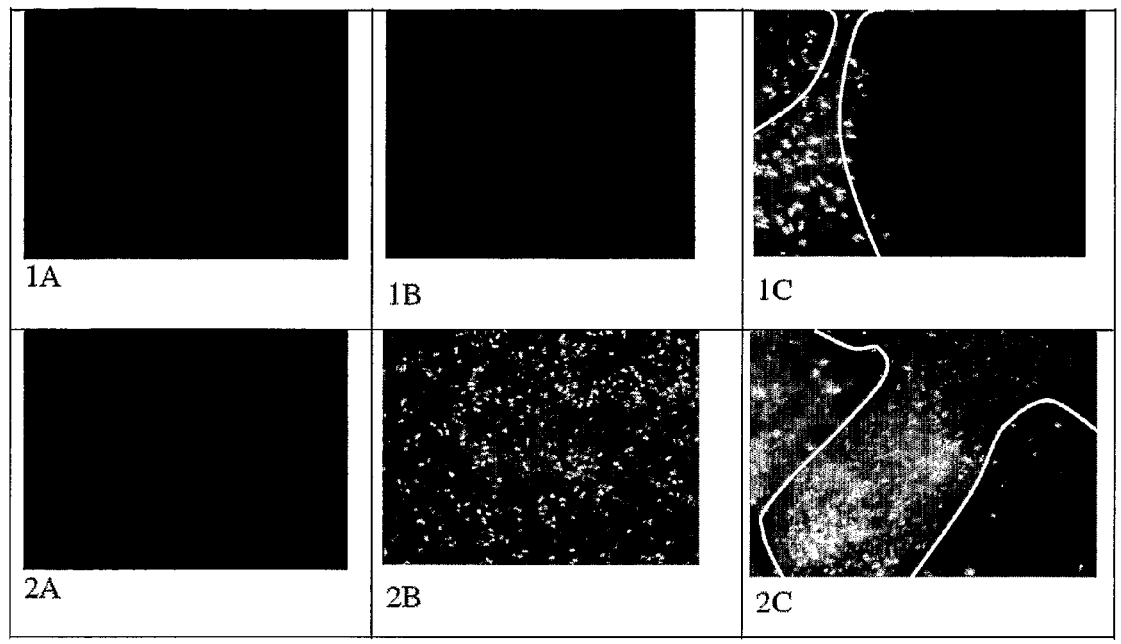
FIG. 16: Glass slides, Epifluorescence Microscopy of *E. coli* K12 immobilised on Qdot treated antibodies. (1A and 2A) Blank slide with no antibodies or Qdots, (1B and 2B) Slide with antibodies but no qdots, (1C and 2C) Slide with antibodies and qdots. Qdot concentration 0.002 µM, antibody concentration of 4 mg/ml. Images 1A to 1C are slides exposed to blue excitation, 2A to 2C are slides exposed to UV excitation. On the slides exposed to blue excitation no cells can be seen on the blank slide (FIG. 16 1A, black) or the slide with immobilised antibodies (FIG. 16 1B, black), however, the slide with the Qdots reveal the cells (FIG. 16 1C). The cells in FIG. 16 1C fluoresce green in the presence of the Qdots (area between the two white lines). The Qdots are the red fluorescing regions of the slide, 1C (area outside the two white lines).
Figure 17:
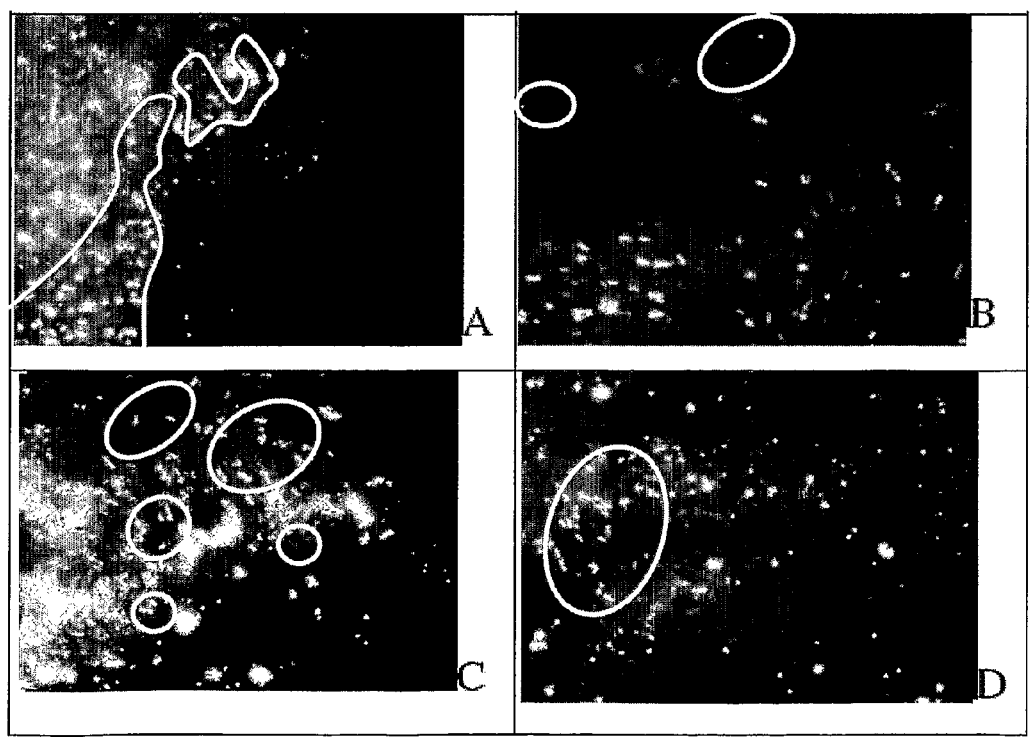

Two band pass filters are used, UV and Blue, and a simple contrast in their effects has been revealed early on. Blue excitation of the cells alone did not excite them to fluoresce, however, UV excitation did, see FIG. 16. FIG. 16A, and C are images taken of cells exposed to a blank slide, a slide with antibodies for the bacteria and a slide with antibodies conjugated to Qdots respectively. Images 1A to 1C are slides exposed to blue excitation, 2A to 2C are slides exposed to UV excitation. On the slides exposed to blue excitation no cells can be seen on the blank slide or the slide with immobilised antibodies, however, the slide with the Qdots reveal the cells. In this case the cells fluoresce green in the presence of the Qdots. The Qdots are the red fluorescing regions of the slide, 1C. FIG. 16 2A shows no bacteria present, possibly due to the absence of antibodies. In 2B of the same figure bacteria are clearly exposed by the UV excitation. This is pictorial evidence that the cells are immobilised by the antibodies and also that the UV excitation reveals the cells without the use of a fluorophore. The reason for this lies with the biomolecules contained within the bacteria, in particular the DNA and aromatic amino acids, well known to fluoresce under UV conditions (autofluorescence). This could be a key in reducing costs of the bead cartridge, but also reveals a certain redundancy of the Qdots. This however, does not reduce the usefulness of the qdots as they can have an accumulating effect on the fluorescence of the bacteria, FIG. 16, 2C. A serial dilution of antibodies is used in FIG. 17. Using Qdots shows that the green fluorescence of the *E. coli* is independent of antibody concentration. Images have been chosen to show fluorescence of the cells as opposed to the immobilising effects of the antibodies. It is also worth noting that after the cells have been exposed to the slides, the slides have been washed vigorously, suggesting that the bond between the antibodies and the cells is a strong bond.

A series of five slides with the usual serially diluted antibodies and a Qdot concentration of 0.002 µM have been assessed for fluorescence under blue and UV excitation, Table 2. The assessment has been based on a score rating between 1 and 5, 5 being the highest fluorescence or immobilisation. UV excitation proved better than blue excitation for both fluorescence and brightness of fluorescence. The assessment has since been repeated with a marked improvement by blue excitation, this is believed to be due to the use of a new batch of antibodies. UV enables the observation of the bacterial auto-fluorescence and it also excites the Qdot fluorescence to fluoresce.

TABLE 2

Assessment of 5 slides with immobilised serial dilution of antibodies and a qdot concentration 0.002 µM

|  | 2 mg/ml | 0.2 mg/ml | 0.02 mg/ml | 0.002 mg/ml |
| --- | --- | --- | --- | --- |
| UV Excitation |  |  |  |  |
| Fluorescence | 3.8 | 3.6 | 3.4 | 3.6 |
| Brightness | 3.2 | 3.6 | 3.6 | 3.4 |
| Immobilisation | 5 | 5 | 5 | 5 |
| Blue Excitation |  |  |  |  |
| Fluorescence | 1.4 | 1.6 | 1.6 | 1.4 |
| Brightness | 1.6 | 1.6 | 1.4 | 1.5 |
| Immobilisation | 5 | 5 | 5 | 5 |

Epifluorescence Microscopy of Bacteria on Glass Beads

Figure 18:
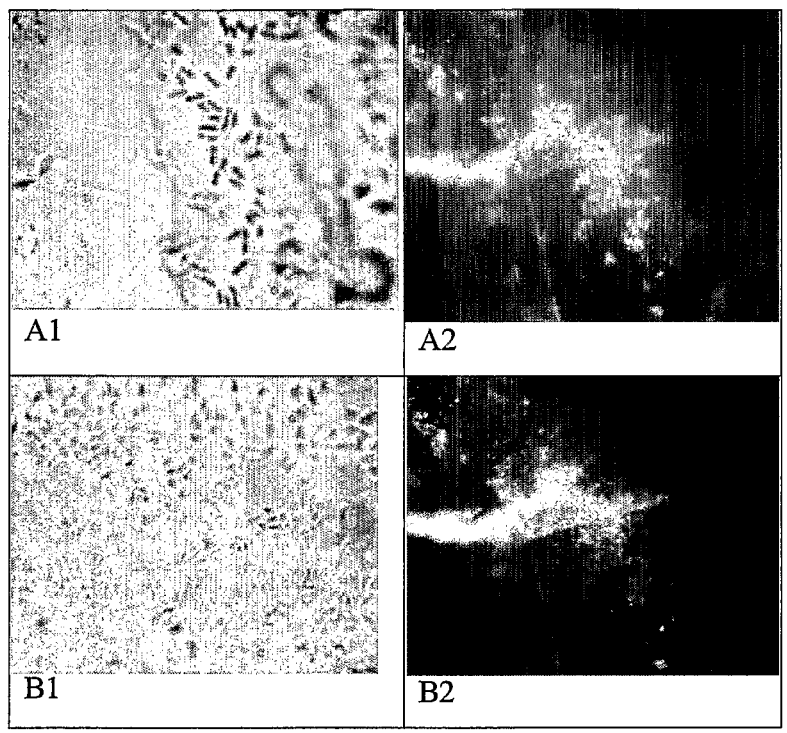
FIG. 18 shows Glass Beads, Epifluorescence Microscopy of *E. coli* K12 immobilised on Qdot (0.002 µM) treated antibodies, ×1000 magnification. Antibody concentration is 4.0 mg/ml. A) Under blue excitation. B) Under UV excitation. A1 and B1 show the cells immobilised onto the glass beads using conventional transmission microscopy. A2 and B2 show the cells under blue light and UV light respectively.

Using epifluorescence microscopy it has been possible to see the immobilised cells on the beads under blue and UV excitation, see FIG. 18. However, resolution of the field of view proves very difficult. This can be appreciated by looking at the images on FIG. 18. The images are in focus at the centre of the field but the perimeter of the field is not resolved, an effect of the bead curvature. However, the images do show that the bacteria can be immobilised. What is also evident and perhaps more important, is that they can be seen. It should be emphasized that the images revealed in this summary do not show the clarity seen on the software when acquired.

Selectivity Results of Antibody Binding

Figure 19:
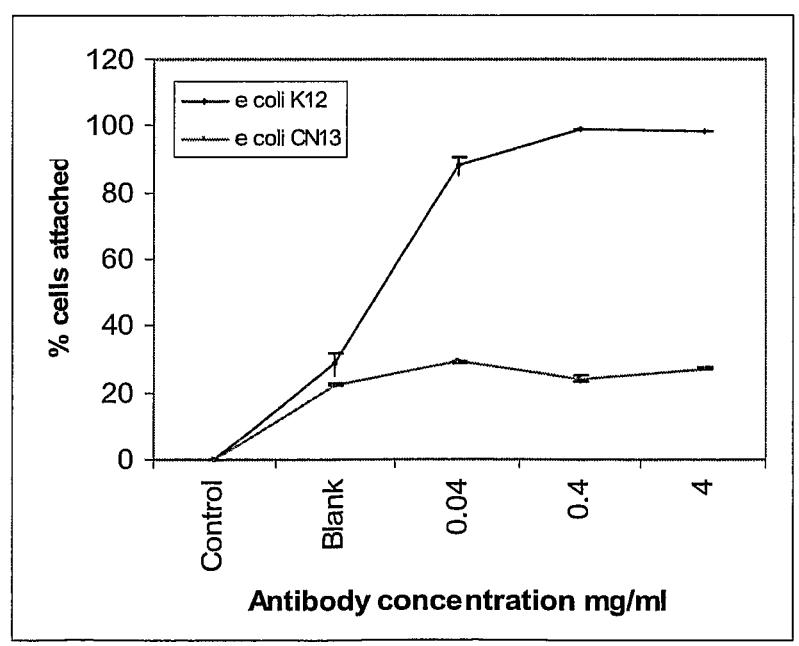
FIG. 19 demonstrates the selectivity of the antibodies directed against *E. coli* K12 in the presence of *E. coli* CN13 strain.

The ability of the immobilised antibodies to selectively attach to contaminants, such as microorganisms is an important property of the device which is demonstrated in the following example. The flow cytometry analysis for cells washed off the prepared glass slides has been repeated using an alternate strain of *Escherichia coli*, CN13. The antibodies used to bind *E. coli* K12 have not been engineered to bind to antigens found on *E. coli* CN 13. Indeed, the levels of CN13 that attached to the prepared glass slides have been vastly reduced in comparison to that of the K12, FIG. 19.

The invention claimed is:

1. A continuous flow device suitable for detecting and/or removing at least one contaminant in a liquid stream, comprising:
   a) at least one cartridge wherein the circumferential wall of said cartridge comprises at least one first inlet and at least one first outlet for said liquid stream and further comprises at least one radiation incident wall portion and at least one radiation emerging wall portion; wherein said cartridge further comprises an optically transparent support material;
      wherein said optically transparent support material is packed in said cartridge such that a liquid stream can pass between voids formed within and/or by said optically transparent support material;
      wherein said optically transparent support material comprises one or more capture molecules for capturing said at least one contaminant, wherein the capture molecules specifically bind to the contaminant,
      wherein said capture molecules are immobilized on the surface of said support material;
      wherein at least one reporter group is connected to each of said capture molecules, wherein said reporter group emits a signal upon binding of said at least one contaminant;
   b) at least one radiation source for emitting a radiation beam for excitation of said reporter group;
   c) at least one detector for detecting said signal emitted by said at least one reporter group.

2. The device of claim 1, wherein said cartridge and said radiation source are movable with respect to each other.

3. The device according to claim 1, wherein the position of said radiation incident wall portion and said radiation emerging wall portion are congruent.

4. The device according to claim 1, wherein the position of said radiation emerging wall portion being opposite to the position of said radiation incident wall portion.

5. The device according to claim 1, wherein said optically transparent support material is composed of beads.

6. The device according to claim 5, wherein said beads are selected from the group consisting of silica, glass and polymer beads.

7. The device according to claim 5, wherein said beads have a diameter between about 1 mm to about 3 cm.

8. The device according to claim 1, wherein said liquid stream is free of particles which can deteriorate the excitation radiation and/or said signal emitted by said at least one reporter group.

9. The device according to claim 1, wherein said at least one reporter group emits a fluorescence or phosphorescence signal after excitation.

10. The device according to claim 1, wherein said at least one reporter group is selected from the group consisting of quantum dots, phosphorescence group, fluorophore groups, complexes comprising of a fluorophore group and a fluorescence-quenching group and mixtures thereof.

11. The device according to claim 1, wherein in addition to said at least one reporter group a second reporter group is comprised which is located in a microorganism to be detected itself (autofluorescence) and is selected from the group consisting of aromatic amino acids, nucleic acids, disulphide bonds and enzymatic co-factors.

12. The device according to claim 1, wherein said capture molecules are selected from the group of antibodies, fragments of antibodies capable of binding a contaminant, aptamers and mixtures thereof.

13. The device according to claim 1, wherein said contaminant is selected from the group consisting of virus, bacteria, cyanobacteria, helminths, protozoa, spores, inorganic molecules, organic molecules and mixtures thereof.

14. The device according to claim 1, wherein said liquid stream is a processed water stream.

15. The device according to claim 14, wherein said processed water stream is selected from the group consisting of wastewater, water from the ballast tank of ships, sea water, river water, brackwater and drinking water.

16. The device according to claim 1, wherein in addition to said at least one capturing molecule enzymes are bound to said surface.

17. The device according to claim 1, wherein the diameter of the excitation radiation is widened by a lens.

18. A continuous flow method suitable for detecting and/or removing of at least one contaminant from a liquid stream using a device according to claim 1, wherein said method comprises directing a liquid stream along or through said device.

19. The method according to claim 18, wherein said temperature and/or said pH of said liquid stream is adjusted to allow detection and/or removal by said capture molecules.

20. The method according to claim 18, wherein said liquid stream has a flow rate between about 100 ml/min to about 21 /min.

21. A cartridge adapted to be used in a continuous flow device suitable for detecting and/or removing at least one contaminant in a liquid stream, wherein said cartridge comprises:
a circumferential wall having at least one first inlet and at least one first outlet for said liquid stream and at least one radiation incident wall portion and at least one radiation emerging wall portion;
wherein said cartridge further comprises optically transparent support material;
wherein said optically transparent support material is packed in said cartridge such that a liquid stream can pass between voids formed within and/or by said optically transparent support material;
wherein said optically transparent support material comprises one or more capture molecules for capturing at least one contaminant, wherein the capture molecules specifically bind to the contaminant,
wherein said capture molecules are immobilized on the surface of said support material;
wherein at least one reporter group is connected to each of said capture molecules, wherein said reporter group emits a signal upon binding of said at least one contaminant.

* * * * *

UNITED STATES PATENT AND TRADEMARK OFFICE
CERTIFICATE OF CORRECTION

PATENT NO.      : 8,454,895 B2
APPLICATION NO. : 12/598627
DATED           : June 4, 2013
INVENTOR(S)     : Gin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 691 days.

Signed and Sealed this
Eighth Day of September, 2015

Michelle K. Lee
*Director of the United States Patent and Trademark Office*